US008388953B2

(12) United States Patent
Gan et al.

(10) Patent No.: US 8,388,953 B2

(45) Date of Patent: Mar. 5, 2013

(54) METHOD OF INCREASING CATHEPSIN B-INDUCED CLEAVAGE OF AMYLOID-β PEPTIDES

(75) Inventors: Li Gan, Burlingame, CA (US); Lennart Mucke, San Francisco, CA (US); Erik Roberson, Vestavia Hills, AL (US); Sarah Mueller-Steiner, Uitikon Waldegg (CH)

(73) Assignee: The J. David Gladstone Institutes, San Francisco, CA (US)

( * ) Notice: Subject to any disclaimer, the term of this patent is extended or adjusted under 35 U.S.C. 154(b) by 96 days.

(21) Appl. No.: 12/826,403

(22) Filed: Jun. 29, 2010

(65) Prior Publication Data

US 2011/0256120 A1 Oct. 20, 2011

Related U.S. Application Data

(63) Continuation of application No. 11/985,601, filed on Nov. 15, 2007, now Pat. No. 7,951,367.

(60) Provisional application No. 60/859,380, filed on Nov. 15, 2006.

(51) Int. Cl.
*A61K 38/43* (2006.01)

(52) U.S. Cl. ........................ 424/94.63; 424/94; 530/350

(58) Field of Classification Search ........................ None
See application file for complete search history.

(56) References Cited

U.S. PATENT DOCUMENTS 5,501,969 A 3/1996 Hastings et al.
2004/0248232 A1 12/2004 Hook

FOREIGN PATENT DOCUMENTS

WO 2004084830 A2 10/2004

OTHER PUBLICATIONS

Walker et al. (Curr. Neuro., vol. 5, pp. 232-243, 2007). Schenk et al. (J. of Medical Chemistry, vol. 38, No. 21, Oct. 13, 1995).*

Morihara et al. (Neuropsychophar., 2005, vol. 30, 1111-1120).*

Tagawa et al. (Biochemical and Biophysical Research Communications, vol. 177, No. 1, pp. 377-387, May 31, 1991).*

Agdeppa et al. (Neurosci., vol. 117, pp. 723-730, 2003).*

Cataldo et al. "Enzymatically Active Lysosomal Proteases are Associated with Amyloid Deposits in Alzheimer Brain" Proc. Natl. Acad. Sci. USA, May 1990, pp. 3861-3865, vol. 87, Medical Sciences.

Cataldo et al. "Increased Neuronal Endocytosis and Protease Delivery to Early Endosomes in Sporadic Alzheimer's Disease: Neuropathologic Evidence for a Mechanism of Increased β-Amyloidogenesis" The Journal of Neuroscience, Aug. 15, 1997, pp. 6142-6151, vol. 17(16), Society for Neuroscience.

Hook et al. "Inhibition of Cathepsin B Reduces β-Amyloid Production in Regulated Secretory Vesicles of Neuronal Chromaffin Cells: Evidence for Cathepsin B as a Candidate β-Secretase of Alzheimer's Disease" Biol. Chem., Sep. 2005, pp. 931-940, vol. 386, Walter de Gruyter.

Hook et al. "Unique Neuronal Functions of Cathepsin L and Cathepsin B in Secretory Vesicles: Biosynthesis of Peptide in Neurotransmission and Neurodegenerative Disease" Biol. Chem., Oct./Nov. 2006, pp. 1429-1439, vol. 387, Walter de Gruyter.

Hook et al. "Neuroproteases in Peptide Neurotransmission and Neurodegenerative Diseases" Biodrugs, 2006, pp. 105-119, vol. 20(2), Adis Data Information.

MacKay et al. "A Possible Role for Cathepsins D, E, and B in the Processing a β-Amyloid Precursor Protein in Alzheimer's Disease" Eur. J. Biochem., 1997, pp. 414-425, vol. 244, FEBS.

Mueller-Steiner et al. "Antiamyloidogenic and Neuroprotective Functions of Cathepsin B: Implications for Alzheimer's Disease" Neuron, Sep. 21, 2006, pp. 703-714, vol. 51, Elsevier Inc.

Wells. Additivity of mutational effects in proteins. Biochemistry. Sep. 18, 1990;29(37):8509-17.

McMahon et al. Using peptide nucleic acids as gene-expression modifiers to reduce beta-amyloid levels. J Mol Neurosci. Aug.-Oct. 2002;19(1-2):71-6.

Banik et al. Inhibition of proteolysis by a cyclooxygenase inhibitor, indomethacin.Neurochem Res., 2000, vol. 25, No. 11, pp. 1509-1515.

Baici et al. Effect of interleukin-1 beta on the production of cathepsin B by rabbit articular chondrocytes. FEBS Lett. Dec. 17, 1990;277(1-2):93-6.

Tagawa et al. Alzheimer's disease amyloid beta-clipping enzyme (APP secretase): identification, purification, and characterization of the enzyme. Biochem Biophys Res Commun.,1991, vol. 177, No. 1, pp. 377-387.

* cited by examiner

*Primary Examiner* — Hope Robinson

(74) *Attorney, Agent, or Firm* — Paula A. Borden; Bozicevic, Field & Francis LLP.

(57) ABSTRACT

The present invention provides a method of increasing cathepsin B-induced cleavage of amyloid-β (Aβ) peptide in a cell or tissue, the method generally involving contacting the cell or tissue with an agent that increases the level of cathepsin B in the cell or tissue. The present invention further provides variant cathepsin B polypeptides that are resistant to inhibition by a cysteine protease inhibitor; as well as nucleic acids encoding the variants, and host cells comprising the nucleic acids.

11 Claims, 12 Drawing Sheets

Fig. 9A

Cathepsin B amino acid sequence alignment

```
mouse        -----------------MWWSLILLSCLLAL----------------------------- 14
rat          -----------------MWWSLIPLSCLLAL----------------------------- 14
chicken      -----------------MSWSRSILCLLGAF----------------------------- 14
human        -----------------MWQLWASLCCLLVL----------------------------- 14
chimpanzee   MEEDGPNVAKMDVGLLWLTLYNIPLIGVFRPMESSLRGLGLQYLVCIDDGQVGSTGKDLC 60
                              :         :   :  .:

mouse        ---------------TSAHDKPSFHPLSDDLINYINKQNTTWQAGRNFYNVDISYLKKLC 59
rat          ---------------TSAHDKPSFHPLSDDMINYINKQNTTWQAGRNFYNVDISYLKKLC 59
chicken      ---------------ANARSIPYYPPLSSDLVNHINKLNTTGRAGHNFHNTDMSYVKKLC 59
human        ---------------ANARSRPSFHPVSDELVNYVNKRNTTWQAGHNFYNVDMSYLKRLC 59
chimpanzee   REPAPWDRWASDLRCSNARSRPSFHPLSDELVNYVNKRNTTWQAGHNFYNVDMSYLKRLC 120
                            :.*:.  *  :  *:*.:::*::** *** :**:**:*.*:**:*:**

mouse        GTVLGGPKLPGRVAFGEDIDLPETFDAREQWSNCPTIGQIRDQGSCGSCWAFGAVEAISD 119
rat          GTVLGGPKLPERVGFSEDINLPESFDAREQWSNCPTIAQIRDQGSCGSCWAFGAVEAMSD 119
chicken      GTFLGGPKAPERVDFAEDMDLPDTFDTRKQWPNCPTISEIRDQGSCGSCWAFGAVEAISD 119
human        GTFLGGPKPPQRVMFTEDLKLPASFDAREQWPQCPTIKEIRDQGSCGSCWAFGAVEAISD 119
chimpanzee   GAFLGGPKPPQRVMFTEDLKLPESFDAREQWPQCPTIKEIRDQGSCGSCWAFGAVEAISD 180
             *:.***** *  ** *  **:.** :**:*:**.:**** :*******************:**

mouse        RTCIHTNGRVNVEVSAEDLLTCCGIQCGDGCNGGYPSGAWSFWTKKGLVSGGVYNSHVGC 179
rat          RICIHTNGRVNVEVSAEDLLTCCGIQCGDGCNGGYPSGAWNFWTRKGLVSGGVYNSHIGC 179
chicken      RICVHTNAKVSVEVSAEDLLSCCGFECGMGCNGGYPSGAWRYWTERGLVSGGLYDSHVGC 179
human        RICIHTNAHVSVEVSAEDLLTCCGSMCGDGCNGGYPAEAWNFWTRKGLVSGGLYESHVGC 179
chimpanzee   RICIHTNAHVSVEVSAEDLLTCCGSMCGDGCNGGYPAEAWNFWTRKGLVSGGLYESHVGC 240
             * *:***.:*.*********:***   ** *******: ** :**.:******:*:**:**
```

Fig. 9B

```
mouse       LPYTIPPCEHHVNGSRPPCTGEG-DTPRCNKSCEAGYSPSYKEDKHFGYTSYSVSNSVKE 238
rat         LPYTIPPCEHHVNGSRPPCTGEG-DTPKCNKMCEAGYSTSYKEDKHYGYTSYSVSDSEKE 238
chicken     RAYTIPPCEHHVNGSRPPCTGEGGETPRCSRHCEPGYSPSYKEDKHYGITSYGVPRSEKE 239
human       RPYSIPPCEHHVNGSRPPCTGEG-DIPKCSKICEPGYSPTYKQDKHYGYNSYSVSNSEKD 238
chimpanzee  RPYSIPP----------------------------------------------------- 247
             .*:***

mouse       IMAEIYKNGPVEGAFTVFSDFLTYKSGVYKHEAGDMMGGHAIRILGWGVENGVPYWLAAN 298
rat         IMAEIYKNGPVEGAFTVFSDFLTYKSGVYKHEAGDVMGGHAIRILGWGIENGVPYWLVAN 298
chicken     IMAEIYKNGPVEGAFIVYEDFLMYKSGVYQHVSGEQVGGHAIRILGWGVENGTPYWLAAN 299
human       IMAEIYKNGPVEGAFSVYSDFLLYKSGVYQHVTGEMMGGHAIRILGWGVENGTPYWLVAN 298
chimpanzee  ------------------------------------------------------------

mouse       SWNLDWGDNGFFKILRGENHCGIESEIVAGIPRTDQYWGRF 339
rat         SWNVDWGDNGFFKILRGENHCGIESEIVAGIPRIQQYWGRF 339
chicken     SWNTDWGITGFFKILRGEDHCGIESEIVAGVPRMEQYWTRV 340
human       SWNTDWGDNGFFKILRGQDHCGIESEVVAGIPRTDQYWEKI 339
chimpanzee  -----------------------------------------
```

METHOD OF INCREASING CATHEPSIN B-INDUCED CLEAVAGE OF AMYLOID-β PEPTIDES

CROSS-REFERENCE

This application is a continuation of U.S. patent application Ser. No. 11/985,601, filed Nov. 15, 2007, and claims the benefit of U.S. Provisional Patent Application No. 60/859,380, filed Nov. 15, 2006, which applications are incorporated herein by reference in their entirety.

STATEMENT REGARDING FEDERALLY SPONSORED RESEARCH

This invention was made with government support under grant number R21 AG024447-01 awarded by the National Institute on Aging. The government has certain rights in this invention.

BACKGROUND

Alzheimer's disease (AD) is a progressive neurodegenerative disorder affecting 7% of the population over 65 years of age and characterized clinically by progressive loss of intellectual function and pathologically by a continuing loss of neurons from the cerebral cortex.

Deposits of amyloid-β (Aβ) peptides surrounded by dystrophic neurites (neuritic plaques) are a hallmark of AD. There are currently no effective therapies for arresting or reversing the impairment of cognitive function that characterizes AD. There is a need in the art for effective therapies for treating AD and related disorders.

LITERATURE

Mueller-Steiner et al. (September 2006) *Neuron* 51:703-714; WO 2004/084830; Hook et al. (2005) *Biol. Chem.* 386: 931-940; Hook (2006) *BioDrugs* 20:105-119; Hook (2006) *Biol. Chem.* 387:1429-1439; U.S. Patent Publication No. 2004/0248232; Cataldo and Nixon (1990) *Proc. Natl. Acad. Sci. USA* 87:3861-3865; Cataldo et al. (1997) *J. Neurosci.* 17:6142; Mackay et al. (1997) *Eur. J. Biochem.* 244:414-425.

SUMMARY OF THE INVENTION

The present invention provides a method of increasing cathepsin B-induced cleavage of amyloid-β (Aβ) peptide in a cell or tissue, the method generally involving contacting the cell or tissue with an agent that increases the level of cathepsin B in the cell or tissue. The present invention further provides variant cathepsin B polypeptides that are resistant to inhibition by a cysteine protease inhibitor; as well as nucleic acids encoding the variants, and host cells comprising the nucleic acids.

BRIEF DESCRIPTION OF THE DRAWINGS

FIGS. 9A and 9B depict an amino acid sequence alignment of cathepsin B amino acid sequences from human (SEQ ID NO:2), chimpanzee (SEQ ID NO:3), mouse (SEQ ID NO:4), rat (SEQ ID NO:5), and chicken (SEQ ID NO:6).

DEFINITIONS

Figure 1A:
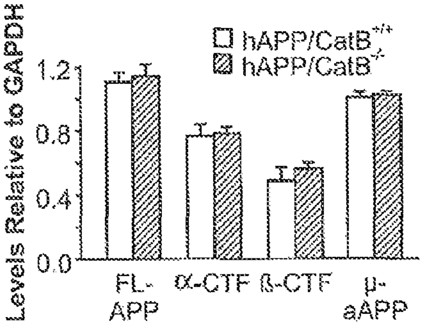
FIGS. 1A-H depict effects of cathepsin B (CatB) on plaque loads and neuronal deficits in hAPP mice.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines, simians, humans, mammalian farm animals, mammalian sport animals, and mammalian pets.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples. In some embodiments, a biological sample will include cells (e.g., neuronal cells; glial cells).

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic polyamines and lipids, including, but not limited to N-(1(2,3-dioleyloxy)propyl)-N,N,N-trimethylammonium chloride (DOTMA) and diolesylphosphotidylethanolamine (DOPE). Liposomes are suitable carriers for gene therapy uses of the invention. Such pharmaceutical compositions should contain a therapeutically effective amount of the compound, together with a suitable amount of carrier so as to provide the form for proper administration to the subject. The formulation should suit the mode of administration.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA; cDNA, DNA-RNA hybrids, or a polymer comprising purine and pyrimidine bases or other natural, chemically or biochemically modified, non-natural, or derivatized nucleotide bases.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis is (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory. Press, Cold Spring Harbor (1989), particularly Chapter 11 and Table 11.1 therein; and Sambrook, J. and Russell, W., Molecular Cloning: A Laboratory Manual, Third. Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tin have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

As used herein the term “isolated” is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term “exogenous nucleic acid” refers to a nucleic acid that is not normally or naturally found in and/or produced by a given bacterium, organism, or cell in nature. As used herein, the term “endogenous nucleic acid” refers to a nucleic acid that is normally found in and/or produced by a given bacterium, organism, or cell in nature.

“Recombinant,” as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems.

Thus, e.g., the term “recombinant” polynucleotide or “recombinant” nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques.

By “construct” or “vector” is meant a recombinant nucleic acid, generally recombinant DNA, which has been generated for the purpose of the expression and/or propagation of a specific nucleotide sequence(s), or is to be used in the construction of other recombinant nucleotide sequences.

“Operably linked” refers to a juxtaposition wherein the components so described are in a relationship permitting them to function in their intended manner. For instance, a promoter is operably linked to a coding sequence if the promoter affects its transcription or expression.

The term “transformation” is used interchangeably herein with “genetic modification” and refers to a permanent or transient genetic change induced in a cell following introduction of new nucleic acid (i.e., DNA exogenous to the cell). Genetic change (“modification”) can be accomplished either by incorporation of the new DNA into the genome of the host cell, or by transient or stable maintenance of the new DNA as an episomal element.

A “host cell,” as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid, and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A “recombinant host cell” (also referred to as a “genetically modified host cell”) is a host cell into which has been introduced a heterologous nucleic acid, e.g., an expression vector.

As used herein, the term “neurons” or “neuronal cells” includes any cell population that includes neurons of any type, including, but not limited to, primary cultures of brain cells that contain neurons, isolated cell cultures comprising primary neuronal cells, neuronal precursor cells, tissue culture cells that are used as models of neurons, and mixtures thereof.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a,” “an,” and “the” include plural referents unless the context clearly dictates otherwise. Thus, for example, reference to “an amyloid beta polypeptide” includes a plurality of such polypeptides and reference to “the agent” includes reference to one or more agents and equivalents thereof known to those skilled in the art, and so forth. It is further noted that the claims may be drafted to exclude any optional element. As such, this statement is intended to serve as antecedent basis for use of such exclusive terminology as “solely,” “only” and the like in connection with the recitation of claim elements, or use of a “negative” limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides a method of increasing cathepsin B-induced cleavage of amyloid-β (Aβ) peptide, and/or Aβ oligomeric aggregates, in a cell or tissue, the method generally involving contacting the cell or tissue with an agent that increases the level of cathepsin B in the cell or tissue. The present invention further provides variant cathepsin B polypeptides that are resistant to inhibition by a cysteine protease inhibitor; as well as nucleic acids encoding the variants, and host cells comprising the nucleic acids.

Methods of Reducing Amyloid-Seta Levels

The present invention provides a method of increasing cathepsin B-induced cleavage of amyloid-β (Aβ) peptide, and/or Aβ oligomeric aggregates, in a cell or tissue, the method generally involving contacting the cell or tissue with an agent that increases the level of cathepsin B in the cell or tissue. The agent contacts a cell that produces cathepsin B, and increases cathepsin B activity levels in the cell and/or cathepsin B activity levels produced by the cell. The agent provides for increased cathepsin B activity levels, which can be achieved by increasing production of cathepsin B by a cell, increasing enzymatic activity of cathepsin B, etc. The cathepsin B will in some embodiments act on Aβ peptide in the same cell in which the cathepsin B is produced. In other embodiments, the cathepsin B is secreted from the cell, and acts on extracellular Aβ protein. Cathepsin B acts on both Aβ protein in monomeric form, and oligomeric Aβ, which may be present in aggregates. In some embodiments, a subject method involves administering to an individual in need thereof an agent that increases the level of cathepsin B in a cell or tissue, where an increased level of cathepsin B in a cell or tissue provides for a reduced level of Aβ in the cell or tissue.

A subject method of reducing Aβ levels generally involves contacting a cell that produces cathepsin B and/or a tissue in which cathepsin B is present (including where the cathepsin B is present extracellularly) with an effective amount of an agent that increases activity, levels of cathepsin B. A therapeutically effective amount of an agent is an amount that, when used in one or more doses, reduces the level of Aβ protein in a cell or tissue by at least about 10%, at least about 20%, at least about 30%, at least about 40%, at least about 50%, at least about 60%, at least about 70%, at least about 80%, or at least about 90%, or more, compared to the level of Aβ protein in the cell or tissue not contacted with the agent. In some embodiments, a therapeutically effective amount of an agent is an amount that, when applied or administered in one or more doses, reduces the level of Aβ monomeric protein in a cell or tissue by at least about 10%, at least about 20%, at least about 30%, at least about 40%, at least about 50%, at least about 60%, at least about 70%, at least about 80%, or at least about 90%, or more, compared to the level of Aβ monomeric protein in the cell or tissue when the agent is not applied or administered. In other embodiments, a therapeutically effective amount of an agent is an amount that, when applied or administered in one or more doses, reduces the level of Aβ oligomeric protein in a cell or tissue by at least about 10%, at least about 20%, at least about 30%, at least about 40%, at least about 50%, at least about 60%, at least about 70%, at least about 80%, or at least about 90%, or more, compared to the level of Aβ oligomeric protein in the cell or tissue when the agent is not applied or administered. In other embodiments, a therapeutically effective amount of an agent is an amount that, when applied or administered in one or more doses, reduces the level of Aβ monomeric and oligomeric protein in a cell or tissue by at least about 10%, at least about 20%, at least about 30%, at least about 40%, at least about 50%, at least about 60%, at least about 70%, at least about 80%, or at least about 90%, or more, compared to the level of Aβ monomeric oligomeric protein in the cell or tissue when the agent is not applied or administered. Monomeric Aβ protein includes $A\beta_{1-42}$ protein. Oligomeric Aβ protein includes aggregates of $A\beta_{1-42}$ protein.

Suitable agents include, but are not limited to, a nucleic acid comprising a nucleotide sequence encoding cathepsin B; a cathepsin B polypeptide; a variant cathepsin B polypeptide that exhibits reduced inhibition by an endogenous inhibitor of cathepsin B (e.g., cystatin C); and a small molecule agent that increases cathepsin B activity levels.

Administering Nucleic Acid

In some embodiments, a subject method for reducing Aβ levels in a cell or tissue involve gene therapy for administering cathepsin B to an individual. Generally, gene therapy can be used to increase (or overexpress) cathepsin B levels in the individual using a recombinant vector to express a nucleic acid encoding cathepsin B, such that cathepsin B polypeptide is produced in a cell of the individual at a higher level than an endogenous level of cathepsin B produced in the cell.

Nucleotide sequences encoding cathepsin B are also known. See, GenBank Accession Nos. BC01240 and M14221. Any known nucleotide sequence encoding cathepsin B can be used. Also suitable for use are nucleotide sequence that vary from a known nucleotide sequence encoding cathepsin B. For example, in some embodiments, a suitable nucleic acid comprises a nucleotide sequence having at least about 75%, at least about 80%, at least about 85%, at least about 90%, at least about 95%, at least about 98%, at least about 99%, or more, nucleotide sequence identity with the nucleotide sequence set forth in GenBank Accession No. BC01240 or M14221 (*Homo sapiens* cathepsin B). In some embodiments, the nucleotide sequence encodes preprocathepsin B (about 339 amino acids). In other embodiments, the nucleotide sequence encodes mature cathepsin B (e.g., amino acids 81-328 of the amino acid sequence depicted in GenBank Accession No. AAH10240 or AAA52129). In some embodiments, a suitable nucleic acid comprises a nucleotide sequence having at least about 75%, at least about 80%, at least about 85%, at least about 90%, at least about 95%, at least about 98%, at least about 99%, or more, nucleotide sequence identity with a nucleotide sequence encoding amino acids 81-328 of the amino acid sequence depicted in GenBank Accession No. AAH10240 or AAA52129.

For example, in some embodiments, a suitable nucleic acid comprises a nucleotide sequence having at least about 75%, at least about 80%, at least about 85%, at least about 90%, at least about 95%, at least about 98%, at least about 99%, or more, nucleotide sequence identity with the nucleotide sequence set forth in SEQ ID NO:1. In some embodiments, a suitable nucleic acid comprises a nucleotide sequence having at least about 75%, at least about 80%, at least about 85%, at least about 90%, at least about 95%, at least about 98%, at least about 99%, or more, nucleotide sequence identity with nucleotides 195-1211 of the nucleotide sequence set forth in SEQ ID NO:1, where nucleotides 195-1211 of the nucleotide sequence set forth in SEQ ID NO:1 encodes amino acids 1-339 of the amino acid sequence set forth in SEQ ID NO:2. In some embodiments, a suitable nucleic acid comprises a nucleotide sequence having at least about 75%, at least about 80%, at least about 85%, at least about 90%, at least about 95%, at least about 98%, at least about 99%, or more, nucleotide sequence identity with nucleotides 435-1178 of the nucleotide sequence set forth in SEQ ID NO:1, where nucleotides 435-1178 of the nucleotide sequence set forth in SEQ ID NO:1 encodes amino acids 81-328 of the amino acid sequence set forth in SEQ ID NO:2.

In some embodiments, the encoded cathepsin B polypeptide has a length of from about 200 amino acids to about 225 amino acids, from about 225 amino acids to about 250 amino acids (e.g., about 248 amino acids), from about 250 amino acids to about 275 amino acids, from about amino acids to about 275 amino acids, from about 300 amino acids, or from about 300 amino acids to about 339 amino acids. The encoded cathepsin B polypeptide is enzymatically active, e.g., the encoded cathepsin B polypeptide truncates $A\beta_{1-42}$ at the C-terminus when brought into contact with $A\beta_{1-42}$ in vitro.

In some embodiments, a suitable nucleic acid comprises a nucleotide sequence encoding an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:2. In some embodiments, a suitable nucleic acid comprises a nucleotide sequence encoding an amino acid sequence having at least about 75%, at least about 80%, at least about 85%, at least about 90%, at least about 95%, at least about 98%, at least about 99%, or more, amino acid sequence identity with amino acids 81-328 of the amino acid sequence set forth in SEQ ID NO:2. FIGS. 9A and 9B depict an amino acid sequence alignment of cathepsin B amino acid sequences from human (SEQ ID NO:2), chimpanzee (SEQ ID NO:3), mouse (SEQ ID NO:4), rat (SEQ ID NO:5), and chicken (SEQ ID NO:6). Conserved amino acid residues are shown. From the alignment depicted in FIGS. 9A and 9B, amino acid sequences that can be varied without significantly adversely affecting function of the protein are readily apparent.

In other embodiments, the cathepsin B-encoding nucleic acid comprises a nucleotide sequence encoding a variant cathepsin B polypeptide, as described in more detail below.

In some embodiments, the cathepsin B-encoding nucleotide sequence is operably linked to a neuron-specific promoter. In other embodiments, the cathepsin B-encoding nucleotide sequence is operably linked to a glial cell-specific promoter. In other embodiments, the cathepsin B-encoding nucleotide sequence is operably linked to a non-neuronal cell-specific promoter.

A cathepsin B nucleic acid can be administered to an individual and/or applied to a cell or tissue, where the nucleic acid is formulated with one or more pharmaceutically acceptable excipients or carriers. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

There are two major approaches to introducing the nucleic acid (e.g., a nucleic acid contained in an expression vector) into the subject's cells for purposes of gene therapy: in vivo and ex vivo. For in vivo delivery, the nucleic acid is introduced directly into the subject. For ex vivo treatment, the subject's cells are removed, the nucleic acid is introduced into the isolated cells and the modified cells are administered to the subject either directly or, for example, encapsulated within porous membranes which are implanted into the subject. See, e.g. U.S. Pat. Nos. 4,892,538 and 5,283,187, both of which are herein expressly incorporated by reference in their entireties.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

Expression vectors may be used to introduce the gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

An example of an in vivo nucleic acid transfer technique includes transfection with viral vectors (such as adenovirus, a lentivirus vector, Herpes simplex I virus, or adeno-associated virus) and lipid-based systems (where useful lipids for lipid-mediated transfer of the gene include DOTMA, DOPE and DC-Chol, for example). In some situations it is desirable to provide the nucleic acid source with an agent that targets the target cells (e.g., a neuronal cell, a glial cell, a non-neuronal cell that produces cathepsin B, etc.), such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., 1987, J Biol Chem, 262:4429-4432; and Wagner et al., 1990, Proc Natl Acad Sci USA, 87: 3410-3414. For a review of the currently known gene marking and gene therapy protocols, see Anderson et al., 1992, Science, 256: 808-813 and WO 93/25673 and the references cited therein.

Administering a Cathepsin B Polypeptide

In some embodiments, a subject method for reducing Aβ levels in a cell or tissue involves contacting the cell or tissue with a cathepsin B polypeptide. In some embodiments, a subject method for reducing Aβ levels in a cell or tissue involves administering to an individual in need thereof an effective amount of a cathepsin B polypeptide.

In some embodiments, the cathepsin B polypeptide has a wild-type amino acid sequence. Amino acid sequences of various cathepsin B polypeptides are known, and any known cathepsin B can be used. See, e.g., Chan et al. (1986) *Proc. Natl. Acad. Sci. USA* 83:7721-7725, for human and mouse preprocathepsin B polypeptides. See also GenBank Accession No. AAH10240 (*Homo sapiens* procathepsin B). Nucleotide sequences encoding cathepsin B are also known. See, e.g., GenBank Accession No. BC01240. Preprocathepsin B polypeptide has a length of about 339 amino acids; mature cathepsin B (amino acids 81-328 of the preprocathepsin B) is about 248 amino acids in length. In some embodiments, the cathepsin B polypeptide that is administered is the mature form.

In some embodiments, the cathepsin B polypeptide has a length of from about 200 amino acids to about 225 amino acids, from about 225 amino acids to about 250 amino acids (e.g., about 248 amino acids), from about 250 amino acids to about 275 amino acids, from about amino acids to about 275 amino acids, from about 300 amino acids, or from about 300 amino acids to about 339 amino acids. The cathepsin B polypeptide is enzymatically active, e.g., the encoded cathepsin B polypeptide truncates $A\beta_{1-42}$, at the C-terminus when brought into contact with $A\beta_{1-42}$ in vitro.

In some embodiments, a suitable cathepsin B polypeptide comprises an amino acid sequence having at least about 75%, at least about 80%, at least about 85%, at least about 90%, at least about 95%, at least about 98%, at least about 99%, or more, amino acid sequence identity with the amino acid sequence set forth in SEQ ID NO:2. In some embodiments, a suitable cathepsin B polypeptide comprises an amino acid sequence having at least about 75%, at least about 80%, at least about 85%, at least about 90%, at least about 95%, at least about 98%, at least about 99%, or more, amino acid sequence identity with amino acids 81-328 of the amino acid sequence set forth in SEQ ID NO:2. FIGS. 9A and 9B depict an amino acid sequence alignment of cathepsin B amino acid sequences from human (SEQ ID NO:2), chimpanzee (SEQ ID NO:3), mouse (SEQ ID NO:4), rat (SEQ ID NO:5), and chicken (SEQ ID NO:6). Conserved amino acid residues are shown. From the alignment depicted in FIGS. 9A and 9B, amino acid sequences that can be varied without significantly adversely affecting function of the protein are readily apparent.

In other embodiments, the cathepsin B polypeptide being administered is a variant cathepsin B polypeptide, as described in more detail below.

Cathepsin B polypeptide can be administered together with a suitable pharmaceutically acceptable carrier or excipient, Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable pharmaceutically acceptable carriers include essentially chemically inert and nontoxic pharmaceutical compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions should contain a therapeutically effective amount of the compound, together with a suitable amount of carrier so as to provide the form for proper administration to the subject. The formulation should suit the mode of administration. For example, oral administration requires enteric coatings to protect the compounds of the invention from degradation within the gastrointestinal tract. In another example, the compounds of the invention may be administered in a liposomal formulation, particularly for nucleic acids, to shield the compounds from degradative enzymes, facilitate transport in circulatory system, and effect delivery across cell membranes to intracellular sites.

In another embodiment, a pharmaceutical composition comprises a cathepsin B protein, and/or one or more additional therapeutic agents; and a pharmaceutically acceptable carrier. In one embodiment, a pharmaceutical composition, comprising a cathepsin B protein, with or without other therapeutic agents; and a pharmaceutically acceptable carrier, is at an effective dose.

A cathepsin B polypeptide can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In some embodiments, a cathepsin B polypeptide composition is formulated in accordance with routine procedures as a pharmaceutical composition adapted for subcutaneous injection or intravenous administration to humans. Typically, pharmaceutical compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

Pharmaceutical compositions adapted for oral administration may be provided, for example, as capsules or tablets; as powders or granules; as solutions, syrups or suspensions (in aqueous or non-aqueous liquids); as edible foams or whips; or as emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semi-solid, or liquid polyols, etc. Solutions and syrups may comprise, for example, water, polyols and sugars.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

Pharmaceutical compositions adapted for parenteral administration include, but are not limited to, aqueous and non-aqueous sterile injectable solutions or suspensions, which may contain antioxidants, buffers, bacteriostats and solutes that render the pharmaceutical compositions substantially isotonic with the blood of an intended recipient. Other components that may be present in such pharmaceutical compositions include water, alcohols, polyols, glycerine and vegetable oils, for example. Compositions adapted for parenteral administration may be presented in unit-dose or multi-dose containers, for example, sealed ampules and vials, and may be stored in a freeze-dried (lyophilized) condition requiring the addition of a sterile liquid carrier, e.g., sterile saline solution for injections, immediately prior to use. Extemporaneous injection solutions and suspensions may be prepared from sterile powders, granules and tablets. Such pharmaceutical compositions should contain a therapeutically or cosmetically effective amount of an active agent, together with a suitable amount of carrier so as to provide the form for proper administration to the subject. The formulation should suit the mode of administration.

Pharmaceutical compositions adapted for transdermal administration may be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols or oils. A topical ointment or cream is used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration may comprise solid carriers such as powders (e.g., having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration may comprise liquid carriers such as, for example, nasal sprays or nasal drops. These pharmaceutical compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In yet another embodiment, cathepsin B may be administered using long-acting cathepsin B formulations that either delay the clearance of cathepsin B from the site or cause a slow release of cathepsin B from, e.g., an injection or administration site. The long-acting formulation that prolongs cathepsin B plasma clearance may be in the form of cathepsin B complexed, or covalently conjugated (by reversible or irreversible bonding) to a macromolecule such as a water-soluble polymer selected from polyethylene glycol) (PEG) and polypropylene glycol homopolymers and polyoxyethylene polyols, i.e., those that are soluble in water at room temperature. See, e.g., U.S. Pat. No. 5,824,642, hereby expressly incorporated by reference in its entirety. Alternatively, the cathepsin B may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides. The polymer need not have any particular molecular weight. In some embodiments, the molecular weight is between about 3500 and 100,000, or between 5000 and 40,000. In some embodiments, the PEG homopolymer is unsubstituted, but it may also be substituted at one end with an alkyl group. In some embodiments, the alkyl group is a C1-C4 alkyl group, e.g., a methyl group. In some embodiments, the polymer is an unsubstituted homopolymer of PEG, a monomethyl-substituted homopolymer of PEG (mPEG), or polyoxyethylene glycerol (POG) and has a molecular weight of about 5000 to 40,000.

Suitable routes and modes of administration of the cathepsin B polypeptide include, but are not limited to, oral, intravenous infusion, subcutaneous injection, intramuscular, topical, depot injection, implantation, time-release mode, intracavitary, intranasal, inhalation, intraocular, and controlled release. The cathepsin B polypeptide also may be introduced parenterally, transmucosally (e.g., orally), nasally, rectally, intravaginally, sublingually, submucosally, intracranially, or transdermally. In some embodiments, administration is parenteral, i.e., not through the alimentary canal but rather through some other route via, for example, intravenous, subcutaneous, intramuscular, intraperitoneal, intraorbital, intracapsular, intraspinal, intrasternal, intra-arterial, or intradermal administration. The skilled artisan can appreciate the specific advantages and disadvantages to be considered in choosing a route and mode of administration.

In one embodiment, a cathepsin B polypeptide is delivered by a controlled-release or sustained release system. For example, the cathepsin B polypeptide may be administered using intravenous infusion, an implantable osmotic pump, a transdermal patch, liposomes, or other modes of administration. In one embodiment, a pump may be used (See, e.g., Langer, 1990, Science 249:1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See, e.g., Langer, Science 249:1527-33 (1990); Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27 International Patent Publication No. WO 91/04014; U.S. Pat. No. 4,704,355). In another embodiment, polymeric materials can be used (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105). Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (see Sidman et al., 1983, Biopolymers, 22:547-556), poly(2-hydroxyethyl methacrylate) (Langer et al., 1981, J. Biomed Mater Res, 15:167-277), and Langer, 1982, Chem Tech, 12:98-105), ethylene vinyl acetate (Langer et al., supra) or poly-D-(−)-3-hydroxybutyric acid (EP 133,988). Sustained-release cathepsin B compositions also include liposomally entrapped cathepsin B. Liposomes containing cathepsin B are prepared by methods known per se; DE 3,218,121; Epstein et al., 1985, Proc Natl Acad Sci USA, 82:3688-3692; Hwang et al, 1980, Proc Natl Acad Sci USA, 77: 4030-4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol percent cholesterol, the selected proportion being adjusted for the optimal cathepsin B therapy.

In yet another embodiment, a controlled release system can be placed in proximity of the target tissue. For example, a micropump may deliver controlled doses directly into the brain, thereby requiring only a fraction of the systemic dose (See, e.g., Goodson, 1984, in *Medical Applications of Controlled Release*, vol. 2, pp. 115-138).

In one embodiment, it may be desirable to administer the agent locally to the area in need of treatment; this may be achieved, for example, and not by way of limitation, by local infusion during surgery, topical application, injection, by means of a catheter, by means of a suppository, or by means of an implant. An implant can be of a porous, non-porous, or gelatinous material, including membranes, such as sialastic membranes, or fibers.

In some embodiments, a cathepsin B polypeptide is formulated and/or delivered in such a way as to facilitate or bypass crossing the blood-brain barrier (BBB). Molecules that cross the blood-brain barrier use two main mechanisms: free diffusion; and facilitated transport. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214-219; Baba et al. (1991) *J. Cereb. Blood Flow Metab.* 11:638-643; and Gennuso et al. (1993) *Cancer Invest.* 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682-684; Pardridge (1991) in: *Peptide Drug Delivery to the Brain*; and Kostis et al. (1994) *J. Clin. Pharmacol.* 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, β-cyclodextrin, α-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, conjugation to a monoclonal antibody (Mab) to the specific carrier molecule transferrin receptor, which facilitated the uptake of the Mab conjugate through the blood-brain barrier, can be carried out. Pardridge (1991); and Bickel et al. (1993) *Proc. Natl. Acad. Sci. USA* 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Other systems and methods that provide for transport of a therapeutic agent such as a protein across the BBB include use of an artificial low-density lipoprotein carrier (U.S. Pat. No. 7,220,833); conjugation of the polypeptide to an oligomer that comprises a lipophilic moiety coupled to a hydrophilic-moiety (U.S. Pat. No. 6,943,148); use of a non-invasive transnasal and transocular drug delivery to the central nervous system using iontophoresis technology, e.g., as described in U.S. Pat. No. 7,200,432; etc.

Small Molecule Agents

In some embodiments, an active agent is a small molecule, e.g., a small organic or inorganic compound having a molecular weight of more than 50 and less than about 2,500 daltons. Agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof.

In some embodiments, the active agent is a non-steroidal anti-inflammatory agent (NSAID). Suitable NSAIDs include, but are not limited to, acetaminophen, salicylate, acetyl-salicylic acid (aspirin, diflunisal), ibuprofen, Motrin, Naprosyn, Nalfon, and Trilisate, indomethacin, glucametacine, acemetacin, sulindac, naproxen, piroxicam, diclofenac, benoxaprofen, ketoprofen, oxaprozin, etodolac, ketorolac tromethamine, ketorolac, nabumetone, and the like, and mixtures of two or more of the foregoing.

A small molecule agent (an "active agent") can be formulated in a composition with one or more pharmaceutically acceptable excipients, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

In the subject methods, the active agent(s) may be administered to the host using any convenient means capable of resulting in the desired increase in cathepsin B activity levels. Thus, the agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules; ointments, solutions, suppositories, injections; inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as, lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. An active agent can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage fauns for injection or intravenous administration may comprise the active agent in a composition as a solution in sterile water, normal saline or another pharmaceutically acceptable carrier.

The term “unit dosage form,” as used herein, refers to physically discrete units suitable as unitary dosages for human and animal subjects, each unit containing a predetermined quantity of compounds, of the present invention calculated in an amount sufficient to produce the desired effect in association with a pharmaceutically acceptable diluent, carrier or vehicle. The specifications for the unit dosage form depend on the particular active agent employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington’s Pharmaceutical Sciences, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Variant Cathepsin B Polypeptides

The present invention provides variant cathepsin B polypeptides, which variants differ from wild-type, native, or endogenous cathepsin B in amino acid sequence, where the difference in amino acid sequence results in resistance of the variant to inhibition by one or more endogenous inhibitor, e.g. an endogenous cysteine protease. The present invention further provides compositions, including pharmaceutical compositions, comprising a variant cathepsin B polypeptide.

A variant cathepsin B polypeptide differs in amino acid sequence by one, two, three, four, five, six, seven, eight, nine, or ten, or more, amino acids from a wild-type cathepsin B amino acid sequence. For example, a subject variant cathepsin B polypeptide differs in amino acid sequence by one, two, three, four, five, six, seven, eight, nine, or ten, or more, amino acids from a polypeptide comprising amino acids 81-328 of the amino acid sequence depicted in GenBank Accession No. AAH10240 or AAA52129 (SEQ ID NO:2).

A subject variant cathepsin B polypeptide exhibits reduced binding affinity to an endogenous inhibitor of cathepsin B cysteine protease activity, compared to the cysteine protease activity of a wild-type, native cathepsin B. For example, a subject variant cathepsin B polypeptide exhibits a binding affinity for an endogenous inhibitor of cathepsin B cysteine protease activity that is from about 10% to about 20%, from about 20% to about 30%, from about 30% to about 40%, from about 40% to about 50%, from about 50% to about 60%, from about 60% to about 70%, from about 70% to about 80%, or from about 80% to about 90% less than the binding affinity to the endogenous inhibitor that is exhibited by the wild-type or other parent cathepsin B polypeptide. The, e.g., a subject variant cathepsin B polypeptide exhibits an at least about 10%, at least about 20%, at least about 30%, at least about 40%, at least about 50%, at least about 60%, at least about 70%, at least about 80%, or at least about 90%, or greater, reduction in binding affinity to an endogenous inhibitor of cathepsin B.

In some embodiments, the endogenous inhibitor is a cystatin, e.g., cystatin C. In other embodiments, the endogenous inhibitor is stefin A.

The variant cathepsin B polypeptide is prepared for storage or administration by mixing variant cathepsin B polypeptide having the desired degree of purity with physiologically acceptable carriers, excipients, or stabilizers. Such materials are non-toxic to recipients at the dosages and concentrations employed. If the variant cathepsin B polypeptide is water soluble, it may be formulated in a buffer such as phosphate or other organic acid salt preferably at a pH of about 7 to 8. If a variant cathepsin B polypeptide is only partially soluble in water, it may be prepared as a microemulsion by formulating it with a nonionic surfactant such as TWEEN™, PLURONICS®, or PEG, e.g., TWEEN™80, in an amount of 0.04-0.05% (w/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The variant cathepsin B to be used for therapeutic administration is sterile. Sterility is readily accomplished by filtration through sterile filtration membranes (e.g., 0.2 micron membranes). The variant cathepsin B ordinarily will be stored in lyophilized form or as an aqueous solution if it is highly stable to thermal and oxidative denaturation. The pH of the variant cathepsin B preparations typically will be about from 6 to 8, although higher or lower pH values may also be appropriate in certain instances. It will be understood that use of certain of the foregoing excipients, carriers, or stabilizers will result in the formation of salts of the variant cathepsin B.

If the variant cathepsin B is to be used parenterally, therapeutic compositions containing the variant cathepsin B generally are placed into a container having a sterile access port, for example, an intravenous solution bag or vial having a stopper pierceable by a hypodermic injection needle.

In some embodiments, the variant cathepsin B polypeptide is formulated and dosed for site-specific delivery. Sustained release formulations may also be prepared, and include the formation of microcapsular particles and implantable articles. For preparing sustained-release variant cathepsin B compositions, the variant cathepsin B can be incorporated into a biodegradable matrix or microcapsule. A suitable material for this purpose is a polylactide, although other polymers of poly-(a-hydroxycarboxylic acids), such as poly-D-(−)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in animal models of the target disorder or, if such models are unavailable, in normal animals. Numerous scientific publications document such animal models.

For obtaining a gel formulation, the variant cathepsin B formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. An exemplary gelling agent is one that is inert to biological systems, nontoxic, simple to prepare, and not too runny or viscous, and will not destabilize the variant cathepsin B held within it.

In some embodiments, the polysaccharide is an etherified cellulose derivative, or one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. In some embodiments, the polysaccharide is methylcellulose.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, it can comprise about 2-5%, more preferably about 3%, of the gel and the variant cathepsin B is present in an amount of about 300-1000 mg per ml of gel.

The dosage to be employed is dependent upon the factors described above. In general, the variant cathepsin B is formulated and delivered to the target site or tissue at a dosage capable of establishing in the tissue a variant cathepsin B level greater than about 0.1 ng/cc up to a maximum dose that is efficacious but not unduly toxic. This intra-tissue concentration should be maintained if possible by continuous infusion, sustained release, topical application, or injection at empirically determined frequencies.

Nucleic Acids, Vectors, and Host Cells

The present invention further provides a nucleic acid comprising a nucleotide sequence encoding a variant cathepsin B polypeptide. A subject nucleic acid comprising a nucleotide sequence encoding a variant cathepsin B polypeptide is referred to herein as a "variant cathepsin B nucleic acid." A subject variant cathepsin B nucleic acid comprises an open reading frame that encodes a subject variant cathepsin B and is capable, under appropriate conditions, of being expressed as a variant cathepsin B polypeptide. Thus, the term encompasses genomic DNA, cDNA, mRNA, and vectors comprising the subject nucleic acid sequences. Also encompassed in this term are nucleic acids that are homologous or substantially similar or identical to the nucleic acids encoding a subject variant cathepsin B.

Vectors

For recombinant production of the variant cathepsin B, the nucleic acid encoding it may be isolated and inserted into a replicable vector for further cloning (amplification of the DNA) or for expression. In another embodiment, the variant cathepsin B may be, produced by homologous recombination, e.g. as described in U.S. Pat. No. 5,204,244. DNA encoding the variant cathepsin B is readily isolated and sequenced using conventional procedures. Many suitable vectors are available. The vector components can include, but are not limited to, one or more of the following: a signal sequence, an origin of replication, one or more marker genes, an enhancer element, a promoter, and a transcription termination sequence, e.g., as described in U.S. Pat. No. 5,534,615.

In some embodiments, the nucleic acid is an expression vector. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest. Numerous suitable expression vectors are known to those of skill in the art, and many are commercially available. The following vectors are provided by way of example; for eukaryotic host cells: pXT1, pcDNA3.1, pSG5 (Stratagene), pSVK3; pBPV, pMSG, and pSVLSV40 (Pharmacia). However, any other plasmid or other vector may be used so long as it is compatible with the host cell.

Depending on the host/vector system utilized, any of a number of suitable transcription and translation control elements; including constitutive and inducible promoters, transcription enhancer elements, transcription terminators, etc. may be used in the expression vector (see, e.g., Bitter et al. (1987) Methods in Enzymology, 153:516-544). In some embodiments, regulatory elements include regulatory elements that result in neuronal cell-specific expression of the operably linked variant cathepsin B polypeptide-encoding nucleic acid. Neuronal cell-specific regulatory elements (including promoters, enhancers, and the like) are known to those skilled in the art. Examples of neuronal cell-specific regulatory elements include those from a neuron-specific enolase (NSE) gene (Hannas-Djebarra et al. (1997) *Brain Res. Mol. Brain. Res.* 46:91-99); a PDGF gene; a Th1 gene (e.g., mouse Thy1.2 (Caroni et al. (1997) *J. Neurosci. Methods* 71:3-9); a neurofilament gene (e.g., NF-L, NF-M, and NF-L); a glial filament acidic protein gene; a myelin basic protein gene; a microtubule associated protein genes; a synaptophysin gene; a tyrosine hydroxylase gene; and the like.

In some embodiments, the variant cathepsin B polypeptide-encoding nucleotide sequence is operably linked to an inducible promoter. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., PBAD (see, e.g., Guzman et al. (1995) J. Bacteriol. 177:4121-4130); a xylose-inducible promoter, e.g., Pxyl (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda PL promoter, a promoter controlled by a heat-sensitive repressor (e.g., CI857-repressed lambda-based expression vectors; see, e.g., Hoffmann et al. (1999) FEMS Microbial Lett. 177(2):327-34); and the like.

In addition, the expression vectors will in many embodiments contain one or more selectable marker genes to provide a phenotypic trait for selection of transformed host cells such as dihydrofolate reductase or neomycin resistance for eukaryotic cell culture.

The variant cathepsin B-encoding nucleotide sequences are typically included in an expression vector that provides for expression of the variant cathepsin B polypeptide-encoding nucleotide sequence and production of the variant cathepsin B polypeptide in a eukaryotic cell. A wide variety of which are known in the art and need not be elaborated upon herein. Vectors include, but are not limited to, plasmids; cosmids; viral vectors; artificial chromosomes (YAC's, BAC's, etc); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject expression vectors, or both.

To generate a genetically modified host cell, a construct comprising a nucleotide sequence encoding a variant cathepsin B polypeptide is introduced stably or transiently into a host cell, using established techniques, including, but not limited to, electroporation, calcium phosphate precipitation, DEAE-dextran mediated transfection, liposome-mediated transfection, heat shock in the presence of lithium acetate, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27.325) are suitable. These examples are illustrative rather than limiting.

In addition to prokaryotes, eukaryotic microbes such as filamentous fungi or yeast are suitable cloning or expression hosts for variant cathepsin B-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces*

*occidentalis*; and filamentous fungi such as, e.g., *Neurospora, Penicillium, Tolypocladium*, and *Aspergillus* hosts such as *A. nidulans* and *A. niger.*

In some embodiments, of particular interest are mammalian cells that normally produce cathepsin B. Examples of such cells include neuronal cells, microglial cells, and astrocytes. Immortalized neuronal cells, microglial cells, and astrocytes are also of interest. Suitable immortalized cells include, but are not limited to, neuro-2A cells; B103; PC12; NT2; and the like. PC12 cells are available from the American Type Culture Collection (ATCC) as ATCC deposit number CRL-1721. Neuro-2a cells are available from ATCC as ATCC deposit number CCL-131.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse. L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

The host cells used to produce a subject variant cathepsin B may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or U.S. Pat. No. 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The variant cathepsin B composition prepared from the cells can be purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available.

Diagnostic Methods

The present invention provides methods for diagnosing AD in an individual. The methods generally involve detecting a level of cathepsin B in an individual, where a level of cathepsin B that is higher than a threshold level indicates that the individual has AD. Levels of cathepsin B are readily determined using any of a variety of assays, including enzymatic assay, immunological assays using antibody specific for cathepsin B, e.g., enzyme-linked immunosorbent assay, radioimmunoassay, a protein ("Western") blot assay, and the like. The level of cathepsin B is detected in a biological sample obtained from an individual. As one example, cathepsin B levels can be detected using the Innozyme Cathepsin B Activity Assay Kit (EMD Biosciences). For example, a fluorogenic peptide substrate is used which provides for a fluorescent signal upon action on the substrate by cathepsin B. Fluorogenic peptide substrates of cathepsin B are known. See, e.g., Stachowiak et al. (2004) *Acta Biochirnica Polonica* 51:81-92; Barrett (1980) *Biochem. J.* 187:909; Non-limiting examples of fluorogenic substrates for cathepsin B include: Benzyloxycarbonyl-phenylalanyl-arginine 4-methyl-7-coumarylamide; and N-benzyloxycarbonyl-L-arginyl-L-arginine 2-naphthylamide.

Subjects Suitable for Treatment

A subject treatment method is suitable for treating an individual in need thereof, e.g., an individual who has been diagnosed as having Alzheimer's disease.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s);

kb, kilobase(s); bp, base pair(s); nt, nucleotide(s); i.m., intramuscular(ly); i.p., intraperitoneal(ly); s.c., subcutaneous(ly); and the like.

Example 1

Cathepsin B cleaves $A\beta_{1-42}$

Here it is demonstrate that CatB actually reduces levels of Aβ peptides, especially the aggregation-prone species Aβ1-42, through proteolytic cleavage. Genetic inactivation of CatB in mice with neuronal expression of familial AD-mutant human amyloid precursor protein (hAPP) increased the relative abundance of Aβ1-42, worsening plaque deposition and other AD-related pathologies. Lentivirus-mediated expression of CatB in aged hAPP mice reduced preexisting amyloid deposits, even thioflavin S-positive plaques. Under cell-free conditions, CatB effectively cleaved Aβ1-42, generating C-terminally truncated Aβ peptides that are less amyloidogenic.

Materials and Methods

Mice $CatB^{-/-}$ mice (129sv) obtained from Dr. Hidde Ploegh (Harvard Medical School, Boston, Mass.) (Deussing et al., 1998) were crossed with hAPP mice (C57BL/6J) from line J20 (Mucke et al., 2000). The first cross resulted in hAPP/$CatB^{+/-}$ mice, which were crossed with $CatB^{+/-}$ (CatB heterozygotes that do not express hAPP) to generate six genotypes: hAPP/$CatB^{-/-}$, hAPP/$CatB^{+/+}$, hAPP/$CatB^{+/+}$, $CatB^{-/-}$, $CatB^{+/+}$, and $CatB^{+/-}$. PCR-based genotyping was performed as described (Deussing et al., 1998; Mucke et al., 2000). We have also generated hAPP/$CX3CR1^{+/GFP}$ mice, which express green fluorescent protein (GFP) in microglia that retain normal fractalkine receptor function (Jung et al., 2000) by crossing hAPP mice with $CX3CR1^{-/-}$ mice with targeted GFP insertion (Dr. D Littman, New York University School of Medicine, New York, N.Y.). All measurements were performed on gender-balanced groups. Anesthetized mice were flush-perfused transcardially with PBS. One hemibrain was fixed in 4% phosphate-buffered paraformaldehyde at 4° C. for 48 h, and the other was stored at −70° C. All experiments were approved by the Committee on Animal Research of the University of California, San Francisco (UCSF).

Immunohistochemistry and Quantitation of Immunoreactive Structures

Sliding microtome sections (30 μm) were prepared for immunohistochemistry. For fluorescence double-labeling, sections were incubated first with rabbit anti-CatB (1:1000, Upstate Biotechnology, Lake Placid, N.Y.), mouse anti-EEA1 (1:50, BD Biosciences, Franklin Lakes, N.J.), mouse mAb anti-Aβ (1:500, 3D6, Elan Pharmaceuticals, South San Francisco, Calif.), mouse anti-APP (8E5, 1:1000, Elan Pharmaceuticals), anti-NeuN (1:1000 Chemicon, Temecula, Calif.), or rabbit anti-GFAP (1:1000, Sigma, St. Louis, Mo.), and then with fluorescein-labeled donkey anti-rabbit (1:300, Jackson ImmunoResearch, West Grove, Pa.) and Texas Red-labeled donkey anti-mouse (1:300, Jackson ImmunoResearch). Microglia were labeled with GFP in the heterozygous $CX3CR1^{+/GFP}$ mice (Jung et all, 2000) that express or do not express hAPP. Amyloid plaques were stained with thioflavin S. High-power immunofluorescence images were obtained by confocal microscopy (Radiance 2000, BioRad, Hercules, Calif.). Lower-power digitized images were acquired with a BX-60 microscope (Olympus, Melville, N.Y.) and Axiovision software (Carl Zeiss, Germany). Areas of fluorescent signal were quantified with ImageJ software (NIH Image). The proportion of CatB-immunoreactive plaques was calculated by dividing the areas occupied by both CatB and either 3D6 or thioflavin S by the area occupied by 3D6 or thioflavin S alone.

Calbindin expression in the dentate gyrus and plaque loads in the hippocampus were quantified as described (Palop et al., 2003). After endogenous peroxidase activity was quenched, sections were incubated with rabbit anti-calbindin (1:15,000, Swant, Bellinzona, Switzerland), biotinylated goat anti-rabbit (1:200, Vector Laboratories, Burlingame, Calif.), or biotinylated mouse monoclonal antibody 3D6 (5 μg/ml, Elan). Binding of the antibody was detected with the Elite kit (Vector Laboratories) using diaminobenzidine and $H_2O_2$ for development. Images were obtained with a DEI-470 digital camera (Optronics, Goleta, Calif.). The integrated optical density from three coronal sections was determined with a Bioquant image analysis system and averaged in two areas of the molecular layer of the dentate gyrus and of the stratum radiatum of the CA-1 region, in which calbindin levels remain stable. Calbindin levels were expressed as the ratio of integrated optical density in the molecular layer and in the stratum radiatum of the CA1. The plaque load was calculated as the percent area of the hippocampus covered by 3D6-immunoreactive material. Three coronal sections were analyzed per mouse, and the average of the individual measurements was used to calculate group means.

Cell Culture and Lentiviral/Adenoviral Infection

Unless otherwise noted, all cell culture supplies, medium, and antibiotics were from Invitrogen (Carlsbad, Calif.). The murine neuronal cell line N2A was maintained in Dulbecco's modified Eagle's medium (DMEM) with 10% heat-inactivated fetal bovine serum (FBS), 100 U/ml penicillin G, and 100 μg/ml streptomycin at 37° C. in a humidified atmosphere containing 5% $CO_2$. Before treatment, the medium was replaced with Neurobasal A medium supplemented with N2, and the cells were treated with fresh Aβ1-42 or Aβ1-40 at various concentrations for 24 h.

For primary neuronal cultures, cortices from mouse pups of different genotypes were isolated on postnatal day 0 or 1. Dissociated cells were plated at 800,000 cells/ml in Neurobasal A medium supplemented with B27, 100 U/ml penicillin G, and 100 μg/ml streptomycin. The genotypes of individual cultures were determined by PCR analysis of the tails of the pups from which the cells were obtained.

Expression of CatB in APP-FAD neurons (hAPP) was inhibited by overexpressing shRNA, which targets endogenous mouse CatB under the U6 promoter. The target sequence was 5'-gaagctgtgtggcactgtc-3' (SEQ ID NO:11). The U6-shRNA expression cassette (pSilencer 1.0, Ambion, Austin, Tex.) was inserted between the PacI and the NheI sites of a modified FUGW (a generous gift of Dr. David Baltimore, California Institute of Technology, Pasadena, Calif., and Dr. Pavel Osten, Max-Planck Institute, Heidelberg, Germany) to generate Lenti-shCatB. A construct expressing a scrambled shRNA was used as a control (Lenti-shSCR). To overexpress CatB, the EGFP expression cassette in FUGW was replaced with mouse CatB cDNA (MGC-6211, ATCC, Manassas, Va.) or nothing to generate Lenti-CatB or Lenti-control. Lentiviral vectors were generated, purified, and titered as described (Chen et al., 2005). Briefly, recombinant lentivirus was generated by cotransfecting the transfer vector with two helper plasmids, delta8.9 (packaging vector) and VSV-G (envelope vector), into 293T cells (American Type Culture Collection) and purified by ultracentrifugation. Viral titers were determined by p24 ELISA (Perkin Elmer, Boston, Mass.) at the UCSF Laboratory of Clinical Virology. After 5 days in culture, cortical neuronal cultures from hAPP pups were infected with Lenti-shCatB to inhibit CatB activity or with Lenti-CatB to elevate CatB activity. Equal amounts of Lenti-shSCR and Lenti-control were used as controls for Lenti-shCatB and Lenti-CatB, respectively. Four days later, supernatants were collected for Aβ1-x and Aβ1-42 ELISA (Johnson-Wood et al. 1997), and cell lysates were harvested for assays of CatB activity (EMD Biosciences, San Diego, Calif.) and protein levels (BCA, Pierce Biotechnology, Rockford, Ill.).

To overexpress hAPP, an adenoviral vector encoding human APP695 cDNA under control of the cytomegalovirus promoter was used to infect neurons cultured from $CatB^{+/+}$ and $CatB^{-/-}$ pups after 5 days in culture. The neurons were initially cultured in B27 and switched to N2 medium by half change on days 2, 3, and 4. On day 7, supernatants and cells were harvested for Aβ ELISA, CatB activity assay, and BCA protein assays.

Stereotaxic Injection of Lentiviral Vectors

The recombinant lentiviral vectors (3 μl, an equivalent of p24~450-200 ng of lentiviral particles) were stereotaxically injected into the hippocampus of hAPP mice at the following coordinates: anterior posterior: −2.2, medial lateral: ±1.8, dorsal ventral: −1.9. To confirm region-specific overexpression of CatB and NEP in hAPP mice, three weeks after injection, mice were flush-perfused transcardially with saline, and brain tissues were rapidly removed. Both hemibrains were postfixed in 4% paraformaldehyde for immunostaining. The contralateral side was marked with a notch before sectioning. The transduction of enzymatically active CatB was confirmed in a cohort of $CatB^{+/-}$ mice three weeks after the injection. The hippocampal lysates were prepared by homogenizing in Cytobuster (Innozyme Cathepsin B Activity Assay Kit, EMD Biosciences) in the absence of protease inhibitors. CatB activity in the ipsilateral hippocampus was compared with that of the contralateral side.

The injection-induced effects on Aβ deposition were expressed as the ratio of the percent area of 3D6-immunoreactive or thioflavin S-positive material on the injected versus the noninjected side: Quantitative analyses were performed with ImageJ software (NIH Image). Three to five coronal sections were analyzed per mouse, and the average ratios were used to calculate group means.

Quantification of Aβ

Snap-frozen hippocampi were homogenized in guanidine buffer, and human Aβ peptides were quantitated by ELISA as described (Johnson-Wood et al., 1997). Human Aβ in the supernatants of primary cortical neurons was also measured by ELISA. The Aβ1-42 ELISA detects only Aβ1-42, and the Aβ1-x ELISA detects Aβ1-40, Aβ1-42, and Aβ1-43, as well as C-terminally truncated forms of Aβ containing amino acids 1-28.

Aβ Preparations and Electron Microscopy

Aβ1-42 and Aβ1-40 were from rPeptide (Athens, Ga.). Aβ powders lyophilized with hexafluoroisopropanol were reconstituted in dry dimethylsulfoxide (Sigma) at a concentration of 5 mM. Aggregated Aβ1-42 was prepared based on protocols developed in previous studies (Dahlgren et al., 2002; Lambert et al., 1998). For protofibrillar Aβ1-42 preparations, DMEM/F-12 was added to achieve a final peptide concentration of 100 μM and incubated at 4° C. for 24 h. For fibrillar conditions, 10 mM HCl was added to achieve a final peptide concentration of 100 μM and incubated for 24 h at 37° C. For unaggregated conditions (fresh Aβ), the 5 mM Aβ in $Me_2SO_4$ was diluted directly into cell-culture medium. For Aβ1-40 aggregation, Aβ1-40 was reconstituted in $H_2O$ at a concentration of 5 mg/ml, and incubated for one week at 37° C.

Aβ1-42 and Aβ1-40 samples were characterized by negative-staining electron microscopy (JEOL 1230, Peabody, Mass.). Samples were prepared with "matured" carbon-coated grids and 2% potassium phosphotungstate, pH 6.5, using the drop method (Hamilton et al., 1980), and examined at 80 KV with a condenser aperture of 200 μm and an objective aperture of 50 μm. Images were obtained with a Gatan Ultrascan USC1000 digital camera (Gatan, Warrendale, Pa.).

In Vitro Cleavage Assay

Different amounts of purified CatB from human liver (Sigma) were preactivated with 4 mM cysteine at room temperature for 5 min in assay buffer, pH 6.0 or 7.0 after adjustment (Cathepsin B Activity Assay Kit, EMD Biosciences). Then, 20 ng of fresh, protofibrillar, or fibrillar Aβ1-42 was added and incubated at 37° C. for 120 min. All samples were run in parallel with and without the specific CatB inhibitor CA074. CatB-induced peptidase cleavage of Aβ1-42 was detected with mass spectrometry. Briefly, 5 μl of the reaction mixture was applied to an NP-20 normal-phase chip (Ciphergen Biosystems, Fremont, Calif.), and the spots were washed with water and air-dried. Twenty percent α-cyano-4-hydroxycinnamic acid in 50% acetonitrile, 0.5% trifluoroacetic acid (2×0.5 μl) was applied, and the chips were allowed to dry. Samples were analyzed in a PBS ITC SELDI-TOF mass spectrometer (Ciphergen) as an average of 160 shots for each spot. The system was calibrated daily with All-in-One peptide standards (Ciphergen) and synthetic Aβ1-42.

The products were also analyzed by western blotting on acid-urea gels with an anti-Aβ antibody (3D6) as described (DeMattos et al., 2001; Esposito et al., 2004) or on a Tricine SDS-PAGE. Briefly, 10 μl of the reaction mixture were resolved on 16% tricine gels and transferred to nitrocellulose membranes. Membranes were labeled with 21F12 (1:2000, Elan Pharmaceuticals), an antibody specific for Aβ1-42, to detect low MW Aβ1-42 oligomers. Since 21F12 was unable to detect higher MW assemblies, 3D6 (1:2000, Elan) was also used for immunoblotting. After incubation with an HRP-conjugated sheep anti-mouse IgG (1:2000; Amersham) secondary antibody, blots were developed with an ECL system (Perkin Elmer).

Quantification of CatB Activities and CatB mRNA

CatB activities in N2A cells or in hippocampus of hAPP mice and their littermate controls were quantified with the Innozyme Cathepsin B Activity Assay Kit (EMD Biosciences), according to the manufacturer's instructions. Cells or hippocampi were lysed in lysis buffer in the absence of proteinase inhibitors, preactivated with 4 mM cysteine, and incubated with the synthetic substrate Z-Arg-Arg AMC at 37° C. for 30 min. Released free AMC was determined fluorometrically as above. The enzymatic activities inhibited by CA074 were defined as CatB-specific activities. Protein concentrations were measured with the BCA protein assay kit (Pierce) and used to normalize CatB activities.

Expression of CatB was measured by quantitative RT-PCR. Total RNA in N2A cells was isolated with Trizol reagent (Invitrogen). After treatment with RNase-free DNase (Ambion) for 30 min at 37° C., total RNA (60 ng/ml) was reverse-transcribed with random hexamers and oligo d(T) primers. The expression of CatB relative to GAPDH was determined with SYBR green dye chemistry and an ABI Prism 7700 sequence detector (Applied Biosystems, Foster City, Calif.), as recommended by the manufacturer. Primer quality was verified by dissociation curve analysis, the slopes of standard curves, and reactions without RT. The following primers were used: mouse CatB (forward 5'-TGGTTTCAG-GTGGAGTCTACA-3' (SEQ ID NO:7); reverse 5'-TG-CACTGGAGAA GGAGATACT-3' (SEQ ID NO:8)) and mouse GAPDH (forward 5'-GGGAAGCCCATCAC- CATCTT-3' (SEQ ID NO:9); reverse 5'-GCCTTCTCCATG-GTGGTGAA-3' (SEQ ID NO:10)).

Statistical Analysis

Statistical analyses were carried out with Graphpad Prism (San Diego, Calif.). For quantification of calbindin and plaque load, experimenters were blinded to the genotypes of the mice. Differences among multiple means were evaluated by ANOVA and the Tukey-Kramer post hoc test. Differences between means were assessed with the unpaired, two-tailed t test or the Mann-Whitney U test. The null hypothesis was rejected at the 0.05 level.

Results

Genetic Ablation of CatB Increases Plaque Deposition and Neuropathology in hAPP Mice To determine the role of CatB in APP processing and Aβ metabolism in vivo, we crossed $CatB^{-/-}$ mice with hAPP mice that produce high levels of Aβ in neurons. CatB activity was undetectable in $CatB^{-/-}$ mice and reduced to 50% of wild-type levels in heterozygotes ($CatB^{+/-}$). Western blot analyses with an anti-hAPP antibody (CT-15) revealed that CatB ablation in hAPP mice did not affect levels of C-terminal fragments (CTF) of hAPP, including α-CTF, β-CTF or full-length hAPP (FL-hAPP) (FIG. 1A). Levels of α-sAPP, detected with 6E10 antibody (Esposito et al., 2004), were not affected by CatB ablation either (FIG. 1A). These results suggest that CatB does not significantly affect the processing of hAPP.

Figure 1B:
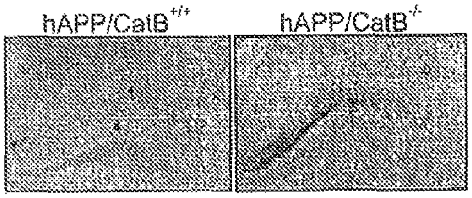
Figure 1C:
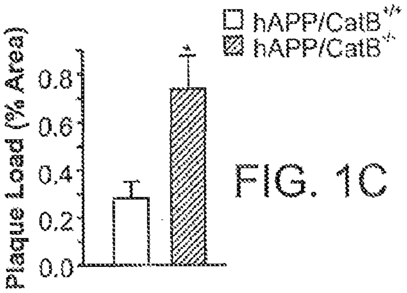
Figure 1D:
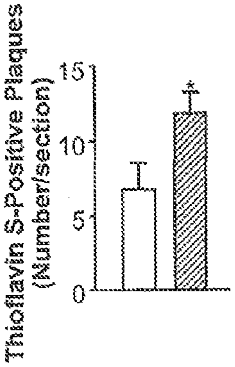
Figure 1E:
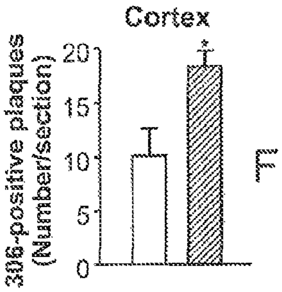
Figure 1F:
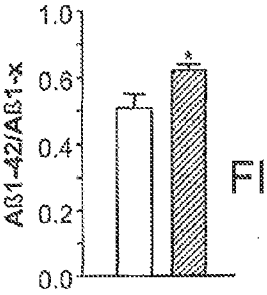

Interestingly, hippocampal plaque loads were significantly higher in hAPP/$CatB^{-/-}$ mice than hAPP/$CatB^{+/+}$ mice at 6 months of age, as shown by immunostaining with an anti-Aβ antibody, 3D6 (FIGS. 1B and 1C). The number of neuritic plaques labeled with thioflavin S was also significantly higher in hippocampi of hAPP/$CatB^{-/-}$ mice than in hAPP/$CatB^{+/+}$ mice (FIG. 1D). In addition, more amyloid deposits were detected in the cortex of hAPP/$CatB^{-/-}$ mice than in hAPP/$CatB^{+/+}$ mice (FIG. 1E). These results indicate that CatB is involved in reducing Aβ deposition. Using an ELISA assay for human Aβ, we next examined the effects of CatB ablation on hippocampal Aβ1-42 and Aβ1-x (approximates total Aβ) levels. Although the increase in the absolute levels of Aβ1-42 and Aβ1-x in hAPP/CatB mice did not reach statistical significance, Aβ1-42/Aβ1-x ratios were significantly higher in hAPP/$CatB^{-/-}$ mice than hAPP/$CatB^{+/+}$ mice at 6-7 months of age (FIG. 1F). This result is consistent with the increased plaque deposition in 6-7-month-old hAPP/$CatB^{-/-}$ mice. In 3-4-month-old hAPP mice before plaque deposition, ablation of CatB did not affect the absolute Aβ1-42 or Aβ1-x levels or the relative abundance of Aβ1-42, suggesting that CatB exerts its anti-amyloidogenic effects during or after the formation of plaques.

Figure 1G:
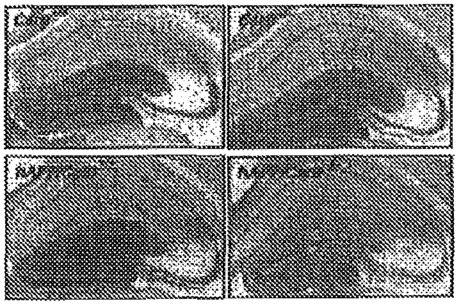
Figure 1H:
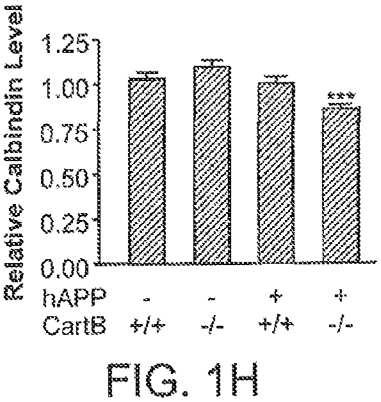

Learning deficits in hAPP mice are influenced by Aβ 1-42 levels and, on an inbred C57BL/6 background, correlated strongly with the depletion of the calcium-binding protein calbindin-D28k in granule cells of the dentate gyms (Palop et al., 2005; Palop et al., 2003). Consistent with their increased levels of Aβ1-42, 6-7-month-old hAPP/$CatB^{-/-}$ mice had significantly lower calbindin levels in the dentate gyrus than age-matched hAPP/$CatB^{+/+}$ mice (FIGS. 1G and H).

These results suggest that CatB reduces plaque deposition and relative Aβ1-42 levels and protects neurons against the Aβ-induced depletion of synaptic activity-dependent proteins.

FIGS. 1A-H. Effects of CatB on Plaque Loads and Neuronal Deficits in hAPP Mice.

(A) Western blot analyses of cortical lysates show comparable levels of FL-hAPP, α-CTF, β-CTF levels, and α-sAPP in APP/$CatB^{+/+}$ and APP/$CatB^{-/-}$ mice (n=9-10/genotype). Levels of hAPP fragments were normalized to those of GAPDH. (B) Photomicrographs of 3D6 immunostaining in the hippocampus of 6-7-month-old hAPP/$CatB^{+/+}$ and hAPP/$CatB^{-/-}$ mice. (C and D) Genetic ablation of CatB increased plaque load in hippocampus (n=10-12/genotype; *, P<0.05, unpaired t test). The amount of Aβ deposits was calculated as the percent area of the hippocampus covered by 3D6-immunoreactive material (C). Thioflavin S-positive neuritic plaques of the entire hippocampus region were counted in seven sections and graphed as average plaque number per section (D). (E) APP/$CatB^{-/-}$ mice have more 3D6-immunoreactive plaques in the cortex than APP/$CatB^{+/+}$ mice. Plaques of the entire cortical region were counted in seven sections and graphed as average plaque number per section (n=10-12/genotype; *, P<0.05, unpaired t test). (F) ELISA measurements of hippocampal levels of Aβ1-42 and Aβ1-x (approximates total Aβ). Ablating CatB increased Aβ1-42/Aβ1-x ratios in 6-7-month-old (n=10-12 mice/genotype; *, P<0.05, unpaired t test). (O) Photomicrographs of calbindin immunostaining in the hippocampus of 6-7-month-old hAPP/$CatB^{+/+}$ mice, hAPP/$CatB^{-/-}$ mice, and littermate controls that do not express human hAPP ($CatB^{+/+}$ and $CatB^{-/-}$). (H) Cabindin levels in the dentate gyrus relative to those in the CA1 regions were significantly lower in hAPP/$CatB^{-/-}$ mice than in hAPP/$CatB^{+/+}$ mice and littermate controls ($CatB^{+/+}$ and $CatB^{-/-}$) (n=10-12/genotype; ***, P<0.001, Tukey Kramer post hoc test). Bars represent means±SEM (A, C, D, E, G).

CatB Accumulates Preferentially within Neuritic Plaques in hAPP Mice

Figure 2A:
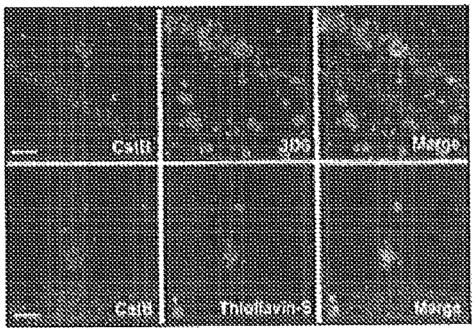
FIGS. 2A-F depict localization of CatB immunoreactivity in hAPP mice.
Figure 2B:
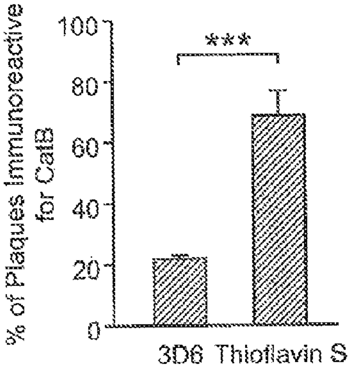

To understand the mechanisms underlying the anti-amyloidogenic and neuroprotective effects of CatB, we characterized the association of CatB with amyloid plaques in 16-20-month-old hAPP mice. Brain sections from hAPP mice were colabeled with a CatB-specific antibody and with either 3D6, which stains both mature and diffuse Aβ deposits, or thioflavin S, which labels the β-sheet structures in mature plaques (FIG. 2A). CatB was present in a subpopulation of 3D6-positive deposits (FIG. 2A) and thioflavin S-positive plaques (FIG. 2A). More thioflavin S-positive than 3D6-positive deposits were immunoreactive for CatB, indicating that CatB accumulates preferentially in mature plaques (FIG. 2B). Anti-CatB immunostaining of brain sections from hAPP/$CatB^{-/-}$ mice yielded no fluorescent signal in 3D6-positive plaques or NeuN-positive neurons, confirming the specificity of CatB antibody. Notably, in 6-7-month-old hAPP/$CatB^{+/+}$ mice, CatB is present in most of the amyloid plaques, consistent with the plaque-reducing effect of CatB in hAPP mice at this age (FIG. 1B-D).

Figure 2C:
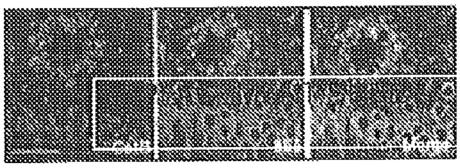
Figure 2D:
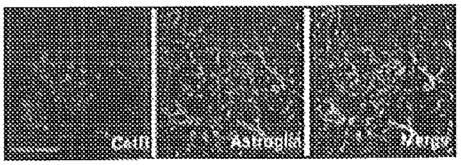
Figure 2E:
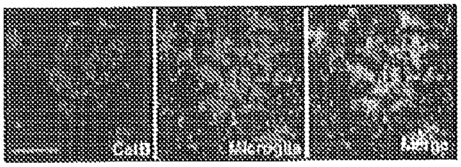

Within neuritic plaques, CatB immunoreactivity overlapped with dystrophic neurites labeled with an anti-hAPP antibody (8E5) (Cheng et al., 2004) (FIG. 2C). These CatB-positive amyloid plaques were also associated with clusters of reactive astroglia labeled with GFAP antibody (FIG. 2D), as well as microglia, as shown by crossing hAPP mice with $CX3CR1^{+/GFP}$ mice, in which microglia are labeled with GFP (FIG. 2E). Interestingly, CatB activity was present in the supernatants of primary cultures enriched for neurons, astrocytes, or microglia; the highest levels were detected in microglial cultures. These results suggest that extracellular CatB accumulating within neuritic plaques could be produced by all three cell types, including activated microglia surrounding the plaques.

Figure 2F:
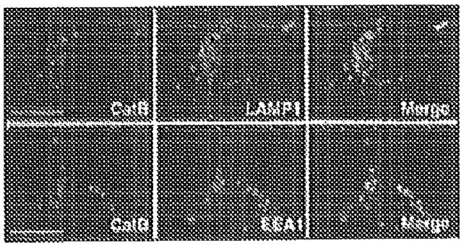

CatB in hippocampal CA1 pyramidal neurons of hAPP mice colocalized with lysosomal membrane glycoprotein 1 (LAMP1), a lysosomal marker (FIG. 2F). CatB also colocalized with endosome-associated autoantigen 1 (EEA-1)-positive early endosomes, a site involved in APP processing and Aβ generation (FIG. 2F). The accumulation of CatB in early endosomes in neurons of vulnerable regions of hAPP brains is consistent with a role of neuronal CatB in modulating Aβ levels.

FIGS. 2A-F. Localization of CatB Immunoreactivity in hAPP Mice (A and B) Colocalization of CatB immunoreactivity with amyloid plaques in 16-20-month-old hAPP mice. (A) Coimmunostaining of an anti-CatB antibody (red) with an anti-Aβ antibody (3D6, green) (upper panel) or with thioflavin S (green) (lower panel). Yellow signal in the merged images represents colocalization of CatB with Aβ peptides (upper panel) or thioflavin S (lower panel). (B) The area occupied by fluorescent signals was quantified with ImageJ software (NIH Image). The proportion of plaques immunoreactive for CatB was calculated by dividing the areas occupied by both CatB and 3D6 or thioflavin-S by the area occupied by 3D6 or thioflavin S alone (n=5; ***, P<0.001, paired t test). (C-E) Confocal image shows partial colocalization (yellow) of CatB (red) with dystrophic neurites labeled with 8E5 (C, green) and astroglia labeled with anti-GFAP (D, green) in the hippocampus of 16-20-month-old hAPP mice. (E) CatB immunoreactivity (red) was also partially associated with microglia (green) in 10-12-month-old hAPP/CX3CR1$^{+/GFP}$ mice. (F) Confocal image shows colocalization (yellow) of CatB (red) with LAMP1 (green, upper panel) or with EEA1 (green, lower panel) in hippocampal neurons of hAPP mice.

CatB Reduces Aβ Levels in Primary Neurons

Figure 3A:
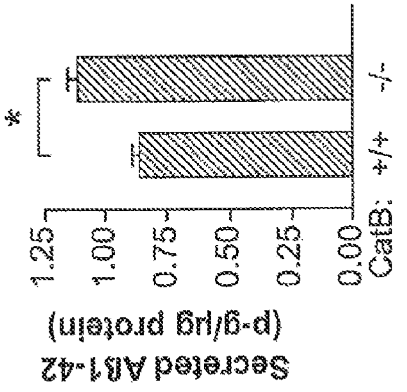
FIGS. 3A-I depict reduction of Aβ levies in primary neurons by CatB.
Figure 3B:
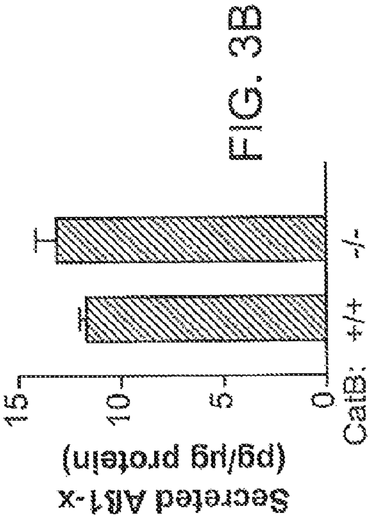

To investigate whether CatB directly affects Aβ levels in neurons, we transduced primary cortical neurons from CatB$^{-/-}$πmice and CatB$^{+/+}$ littermate controls with an adenoviral vector expressing hAPP. Aβ1-42 levels were significantly higher in the supernatants from CatB$^{-/-}$ neurons than CatB$^{+/+}$ neurons (FIG. 3A). Lack of CatB did not increase Aβ1-x levels in these cultures (FIG. 3B).

Figure 3C:
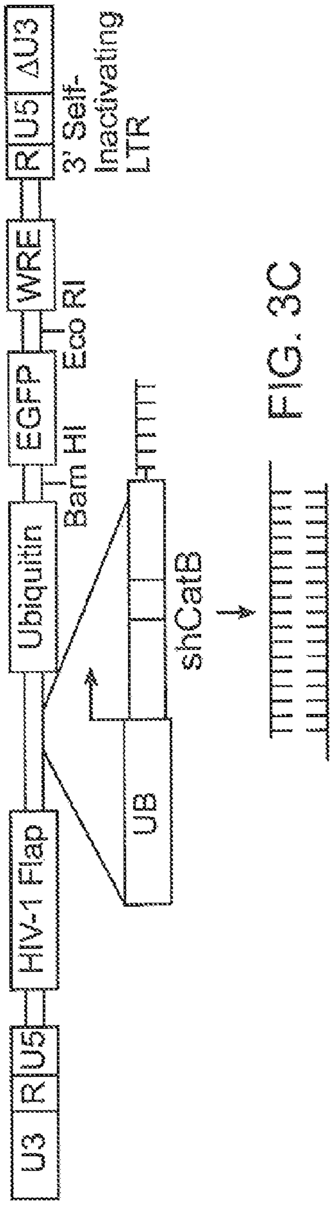
Figures 3D, 3E, 3F, 3G, 3H, 3I:
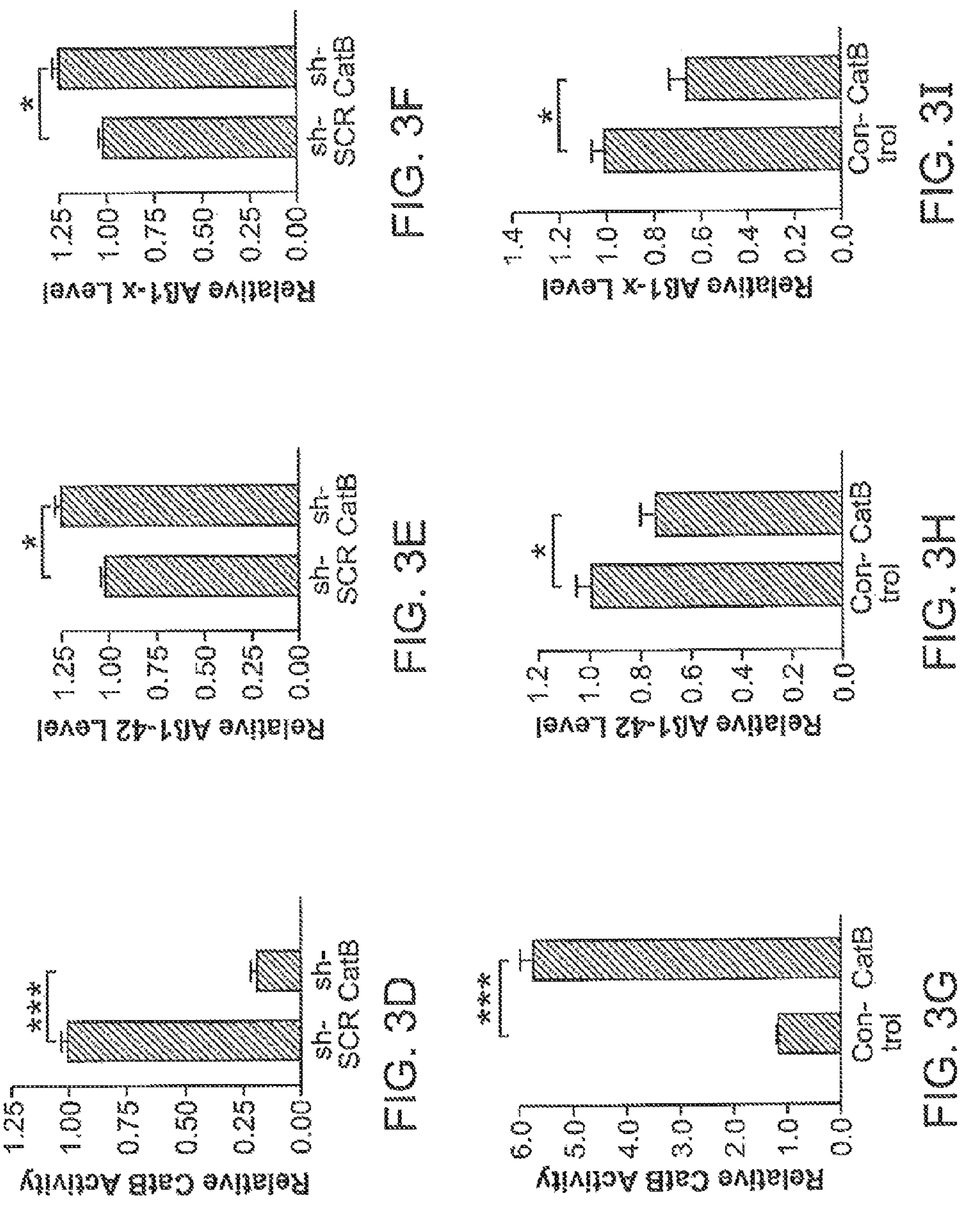

In complementary experiments, we inhibited CatB expression in primary cortical neuronal cultures from hAPP mice with a lentiviral vector encoding a small-hairpin RNA targeting CatB (Lenti-shCatB) (FIG. 3C). CatB activity was significantly lower in cultures expressing Lenti-shCatB than in cultures expressing a scrambled shRNA (Lenti-shSCR) (FIG. 3D). Inhibiting, CatB significantly increased Aβ1-42 levels, suggesting that CatB negatively regulates Aβ1-42 levels (FIG. 3E). Aβ1-x levels were also significantly elevated in cultures infected with Lenti-shCatB, indicating that CatB also reduces total Aβ levels (FIG. 3F).

To further confirm the negative effects of CatB on Aβ levels, we increased CatB activity in primary neuronal cultures from hAPP mice with a lentiviral vector encoding mouse CatB cDNA (Lenti-CatB): Infection with Lenti-CatB resulted in significant increase in CatB activity (FIG. 3G). Both Aβ1-42 and Aβ1-x levels were significantly reduced in cultures overexpressing CatB (FIGS. 3H and I).

FIGS. 3A-I. CatB Reduces Aβ Levels in Primary Neurons

Levels of human Aβ1-x and Aβ1-42 in the supernatants were determined with an Aβ ELISA and normalized to the protein concentrations in the cell lysates. Bars represent means±SEM (A-B, D-I). (A and B) Levels of Aβ1-42 (A), but not Aβ1-x (B), were significantly higher in CatB$^{-/-}$ neurons (n=6) than in CatB$^{+/+}$ neurons (n=8) infected with hAPP adenovirus. *, P<0.05, Mann-Whitney U test. (C-F). (C-F) Inhibition of CatB increased Aβ levels in hAPP primary neurons. Diagram (not to scale) of the lentiviral vector Lenti-shCatB, which expresses both. EGFP and shCatB (C). CatB activities (D) were significantly lower in hAPP neurons infected with Lenti-shCatB than in those infected with the control lentiviral vector expressing scrambled shRNA (Lenti-shSCR) (n=15; ***, P<0.001, unpaired t test). Levels of Aβ1-42 (E) and Aβ1-x (F) were significantly higher in cultures infected with Lenti-shCatB than in those infected with Lenti-shSCR (n=15; *, P<0.05, unpaired t test). Average Aβ levels in Lenti-shSCR-infected cultures were arbitrarily set as 1. (G-I) Overexpression of CatB decreased Aβ levels in hAPP primary neurons. CatB activities (G) were significantly increased in hAPP neurons infected with Lenti-CatB (n=4, ***, P<0.001, unpaired t test). Levels of Aβ1-42 (H) and Aβ1-x (1) were significantly lower in cultures infected with Lenti-CatB than in those infected with equal amounts of Lenti-control (n=4; *, P<0.05, unpaired t test). Average Aβ levels in Lenti-control-infected cultures were arbitrarily set as 1.

CatB is Increased in Aβ1-42-Treated Neuronal Cells and in Brains of hAPP Mice

Figure 4A:
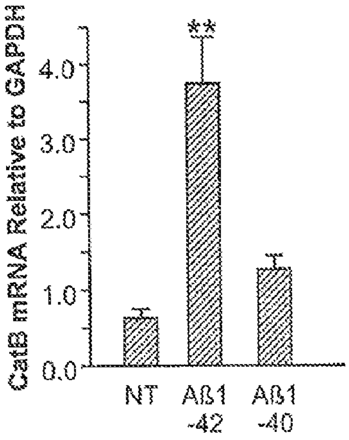
FIGS. 4A-D depict upregulation of CatB by $Aβ_{1-42}$ in N2A cells and in young and middle-aged hAPP mice.
Figure 4B:
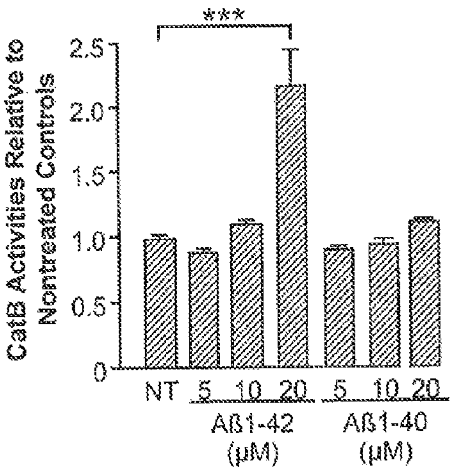
Figure 4C:
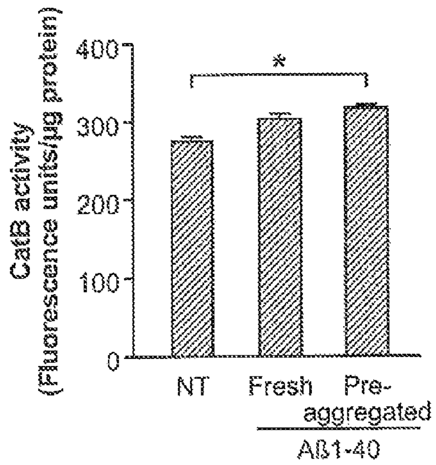

Our results so far demonstrate that levels of Aβ, including Aβ1-42, are down-regulated by CatB in hAPP mice and primary neuronal cultures. Notably, elevated levels of Aβ1-42 stimulate microglia to express more CatB mRNA (Gan et al., 2004). To determine if Aβ1-42 also regulates CatB in neuronal cells, where the majority of Aβ is made, we stimulated neuroblastoma (N2A) cells with increasing amounts of Aβ1-42 and Aβ1-40. Both CatB mRNA levels (FIG. 4A) and enzymatic activities (FIG. 4B) were markedly increased by Aβ1-42; Aβ1-40 had little or no effect. Treatment with pre-aggregated Aβ1-40, however, induced a modest but significant increase in CatB activity, supporting the notion that regulation of CatB is influenced by the assembly states of Aβ peptides (FIG. 4C).

Figure 4D:
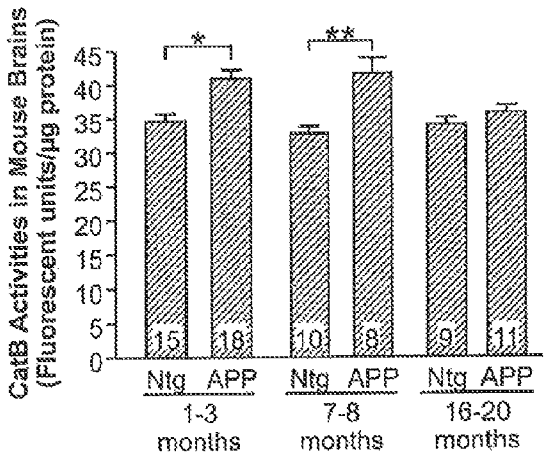

To determine if Aβ levels modulate CatB activities in vivo, we compared the enzymatic activities of CatB in the hippocampus of hAPP mice. Compared with age-matched nontransgenic controls, CatB levels were higher in hAPP mice both before (1-3 months) and after (7-8 months) plaque deposition (FIG. 4D), suggesting that the hAPP/Aβ-induced increase in CatB activities does not depend on insoluble Aβ deposits in vivo. At 16-20 months, CatB activities were similar to those in nontransgenic controls, indicating that hAPP/Aβ failed to stimulate CatB at old age (FIG. 4D).

FIGS. 4A-D. Upregulation of CatB by Aβ1-42 in N2A Cells and in Young and Middle-Aged hAPP Mice (A-C) N2A cells were treated with increasing amounts of nonaggregated Aβ1-42 or Aβ1-40 for 24 h and harvested for quantitative RT-PCR and CatB activity assays. NT, non-treated. CatB mRNA levels (A) and CatB enzymatic activities (B) were significantly elevated by 20 μM Aβ1-42; Aβ1-40 had little effect. (C) Preaggregated Aβ1-40 (20 μM) had a modest but significant effect. Bars represent means±SEM (n=4-6; , P<0.01. *, P<0.001. *, P<0.05, Tukey Kramer post hoc test). (D) CatB activity levels were significantly higher in young (1-3 months) and middle-aged (7-8 months), but not elderly (16-20 months) hAPP mice, than in age-matched nontransgenic (ntg) controls. Bars represent means±SEM (n=8-18, *, P<0.05, **, P<0.01, Tukey Kramer post hoc test).

CatB Mediates C-terminal Truncations of Aβ1-42 in Vitro

Figure 5B:
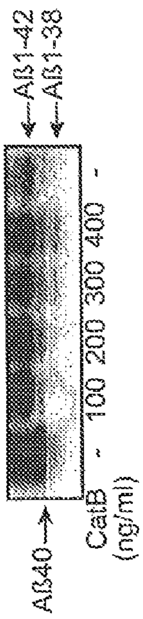
FIGS. 5A-G depict CatB-induced C-terminal truncation of $Aβ_{1-42}$.
Figure 5C:
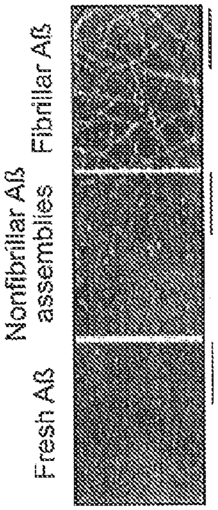
Figure 5A:
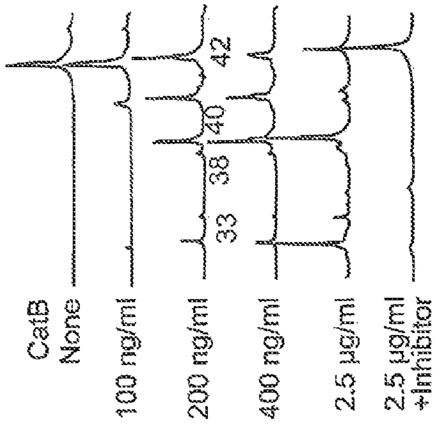

Since the relative abundance of Aβ1-42 was increased in the hippocampus of hAPP/CatB$^{-/-}$ mice and in CatB$^{-/-}$ neurons overexpressing hAPP, we hypothesized that Aβ1-42 is a substrate for CatB and that CatB reduces levels of Aβ1-42 through proteolytic cleavage. Under cell-free conditions, synthetic Aβ1-42 was incubated with purified CatB at pH 6.0, a pH close to that of endosomes, where CatB is likely to encounter Aβ intracellularly (Cataldo et al., 1997; Hook et al., 2002) (FIG. 1F). The proteolytic products were analyzed with SELDI-TOF mass spectrometry. Incubating Aβ1-42 with CatB resulted in the dose-dependent generation of Aβ1-40, Aβ1-38, and Aβ1-33 through proteolytic cleavage at $Val_{40}$-$Ile_{41}$, $Gly_{38}$-$Gly_{39}$, and $Gly_{33}$-$Leu_{34}$ (FIG. 5A). No truncations occurred in the presence of the inhibitor CA074 or in the absence of CatB, confirming that the truncations were dependent on the proteolytic activity of CatB. Increasing the concentration of CatB decreased Aβ1-42 and increased Aβ1-38 (FIG. 5A). The dose-dependent cleavage of Aβ1-42 was confirmed by western blot analysis of acid-urea gels (FIG. 5B). Levels of Aβ1-40 were increased initially at lower doses (100-400 ng/ml; but decreased at higher doses (0.4-2.5 μg/ml) (FIG. 5A). These results indicate that CatB acts as a carboxydipeptidase that cleaves Aβ1-42 at the C-terminus to generate Aβ1-40, which in turn serves as a substrate for the generation of Aβ1-38.

Figure 5D:
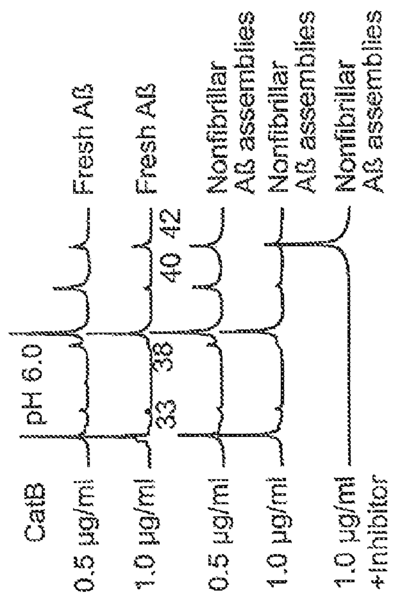

Although CatB did not appear to completely degrade Aβ peptides, Aβ1-33 was also generated (FIGS. 5A and 5D) in a dose-dependent manner, presumably by endopeptidase activity. Consistent with the weaker endopeptidase than carboxydipeptidase activity of CatB at acidic pH (4.0-6.0) (Musil et al., 1991; Nagler et al., 1997), higher concentrations of CatB were required to generate Aβ1-33 than to generate Aβ1-40 and Aβ1-38 (FIG. 5A). Interestingly, even when Aβ1-40 was almost completely converted to Aβ1-38, no Aβ1-36 was generated from Aβ1-38, indicating that Aβ1-38 is not a substrate for CatB's carboxydipeptidic activity. Thus, CatB may counteract amyloidosis by catalyzing the sequence-specific C-terminal truncation of Aβ 1-42.

CatB Cleaves Aggregated Aβ1-42 and Reduces Levels of Aβ Fibrils in Vitro

Next, we investigated whether CatB also cleaves soluble and insoluble Aβ1-42 assemblies. Protofibrillar and fibrillar preparations of Aβ1-42 were confirmed with negative-staining electron microscopy (FIG. 5C). Protofibrils of Aβ1-42 were highly toxic in cultured primary neurons (Chen et g., 2005; Hartley et al., 1999) and, at pH 6.0, were cleaved by CatB as efficiently as nonaggregated preparations, resulting in the same C-terminally-truncated peptides, Aβ1-40, Aβ1-38, and Aβ1-33 (FIG. 5D), which are less toxic and fibrillogenic than Aβ1-42 (Iijima et al., 2004; Zhang et al., 2002). Incubation of CatB induced a marked decrease in the amounts of high-molecular-weight (MW) Aβ assemblies, as shown on Tricine SDS-PAGE gels. Levels of low-MW Aβ1-42 oligomers and monomers, detected with an antibody specific for Aβ1-42, were also reduced. Inclusion of the CatB inhibitor CA074 significantly diminished such effects (FIG. 5E). These results suggest that CatB effectively targets Aβ assemblies in vitro.

Figure 5F:
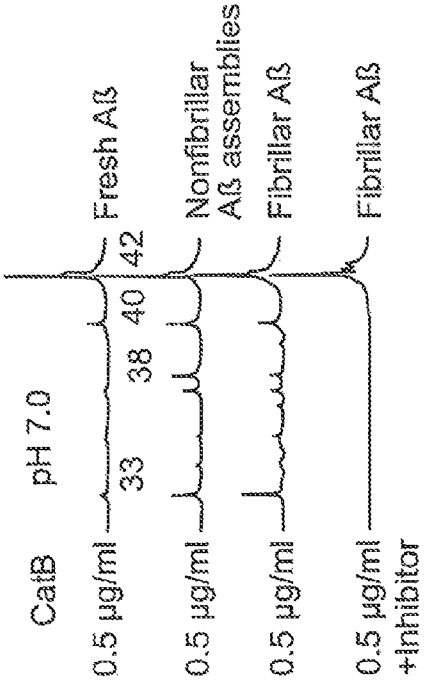
Figure 5E:
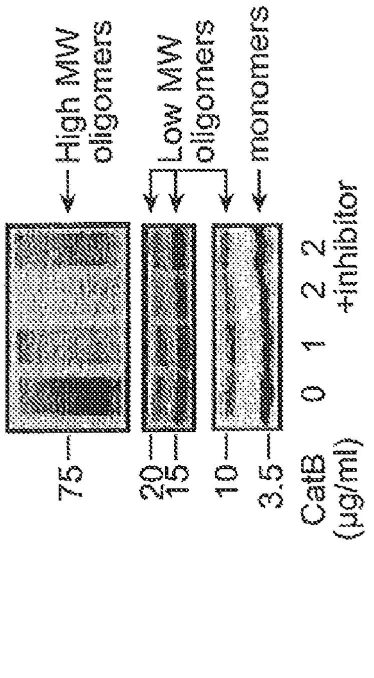
Figure 5G:
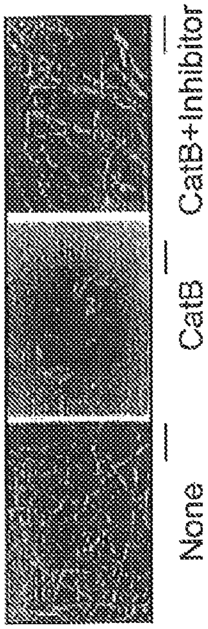

At neutral pH (~7.0), the ability of CatB to cleave Aβ, especially nonaggregated (fresh) Aβ, was markedly reduced (FIG. 5F). Nevertheless, protofibrillar/nonfibrillar Aβ oligomers and fibrillar Aβ1-42 preparations were cleaved by CatB even at neutral pH, resulting in the same truncated Aβ species observed at pH 6.0 (FIGS. 5A and 5F). The ability of CatB to cleave even aggregated Aβ1-42 suggested that CatB might be able to reduce preformed Aβ fibrils. Indeed, incubation of fibrillar Aβ1-42 with CatB did reduce the amount of fibrillar structures (FIG. 5G). This effect depended on the proteolytic activity of CatB, as demonstrated by inhibition with CA074 (FIG. 5G).

FIGS. 5A-G. CatB-Induced C-Terminal Truncation of Aβ1-42

CatB-specific activity was abolished by its inhibitor (CA074). Similar results were obtained in 2-5 independent Aβ preparations. (A) Seidi-TOF mass spectrometry analysis of dose-dependent cleavage of fresh Aβ1-42 (nonaggregated) by pure CatB (100-2500 ng/ml) at pH 6.0. (B) A western blot of an acid-urea gel shows dose-dependent generation of Aβ1-40 and Aβ1-38 from Aβ1-42. Uncleaved Aβ1-42 and Aβ1-40 peptides served as MW controls. (C) Photomicrograph of fresh, protofibrillar, and fibrillar Aβ1-42 preparations visualized with negative-staining electron microscopy. Scale bar: 200 nm. (D and F) Seldi-TOF mass spectrometry analysis of CatB-induced cleavage of aggregated Aβ1-42 (protofibrillar and fibrillar). Protofibrillar Aβ1-42 was cleaved as efficiently as fresh Aβ1-42 at pH 6.0 (D). CatB induced cleavage of fresh, protofibrillar, and fibrillar Aβ1-42 at pH 7.0 (F). (E) A western blot of Tricine gel (16%) shows effects of CatB (1-2 μg/ml) on Aβ1-42 assemblies, including high MW Aβ oligomers, and putative monomeric, dimeric, trimeric, and tetrameric Aβ1-42 (arrows), in the presence or absence of CA074, according to the MW markers (3.5-75 kDa). (G) Electron microscopy photomicrograph of preformed Aβ1-42 fibrils incubated with CatB in the presence or absence of its inhibitor CA074. Scale bar: 200 nm.

CatB Gene Transfer Reduces Amyloid Plaques in Aged hAPP Mice

Figure 6A:
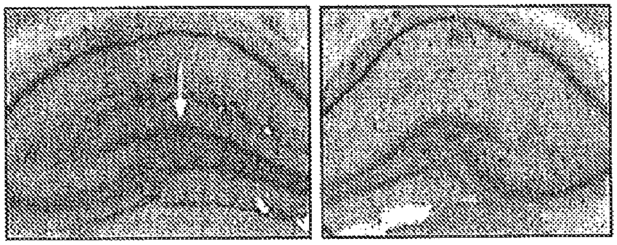
FIGS. 6A-F depict reduction of amyloid plaques by CatB gene transfer in aged hAPP mice.
Figure 6B:
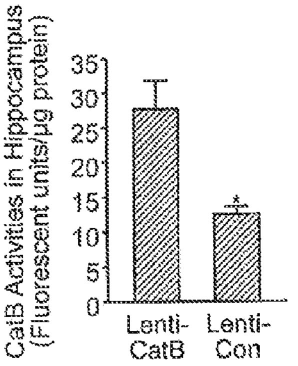

The ability of CatB to cleave Aβ1-42 aggregates and the accumulation of CatB within amyloid plaques support the notion that CatB might reduce established plaques in aged hAPP mice. To test this hypothesis, we injected Lenti-CatB, the vector we used to increase CatB levels in primary neuronal cultures (FIG. 3G), into the hippocampus of 12-15-month-old hAPP mice, which have significant plaque deposition. Lenti-control, which does not encode a functional protein, served as a negative control for nonspecific viral effects. A lentiviral vector overexpressing NEP (Lenti-NEP) (Marr et al., 2003) served as a positive control. Three weeks after the stereotaxic injections, CatB immunoreactivity (FIG. 6A) and enzymatic activity (FIG. 6B) were much stronger in the injected hippocampus, especially in the dentate gyrus, than that in the contralateral side. Lenti-NEP also induced higher NEP immunoreactivity in the dentate gyrus (data not shown).

Figure 6C:
Figure 6D:
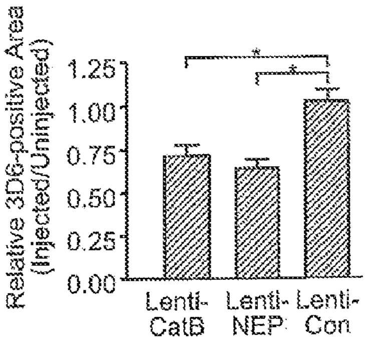
Figure 6E:
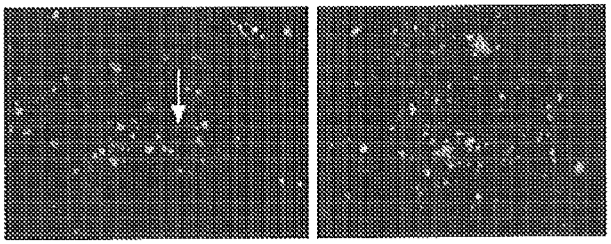
Figure 6F:
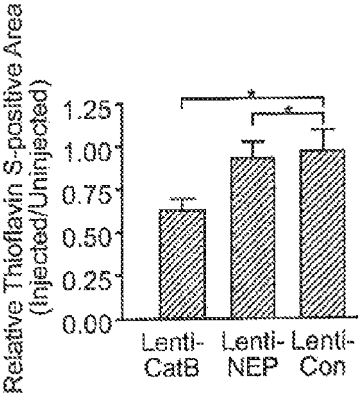

Injection of Lenti-CatB (FIG. 6C) or Lenti-NEP significantly reduced 3D6-positive Aβ deposits in the ipsilateral dentate gyrus; control virus had no effect (FIG. 6D). These results suggest that, in aged hAPP mice, CatB reduces preexisting plaque load as effectively as NEP. Notably, CatB gene transfer markedly reduced thioflavin S-positive neuritic plaques (FIGS. 6E and 6F), whereas Lenti-NEP did not (FIG. 6F). Thus, CatB was more effective than NEP in removing aggregated Aβ in established dense mature amyloid plaques.

FIGS. 6A-F. CatB Gene Transfer Reduces Amyloid Plaques in Aged hAPP Mice

All stereotaxic injections were performed on the left side; the uninjected right side served as an internal control. (A) Representative CatB immunostaining of the Lenti-CatB-injected (left) and uninjected (right) hippocampus in a 12-15-month-old hAPP mouse. (B) CatB enzymatic activities in hippocampi of $CatB^{-/-}$ mice after injection of Lenti-CatB or Lenti-Control (n=3 mice/group; *, P<0.05, unpaired t test). (C) Representative 3D6 immunostaining of the Lenti-CatB-injected (left) and uninjected (right) hippocampus in a 12-15-month-old hAPP mouse. (D) Reduction of 3D6-immunoreactive Aβ deposits in the hippocampus of 12-15-month-old hAPP mice after injection of Lenti-CatB (12 mice) or Lenti-NEP (7 mice), but not Lenti-Control (5 mice). For each mouse, the extent of hippocampal Aβ deposits was expressed as the ratio between the percent area occupied by 3D6 immunoreactivity on the injected versus uninjected side. *, P<0.05, Tukey Kramer post hoc test. (E) Representative photomicrograph of thioflavin-S staining of the Lenti-CatB-injected (left) and uninjected (right) hippocampus in a 12-15-month-old hAPP mouse. (F) Reduction of thioflavin S-positive plaques in the hippocampus of 12-45-month-old hAPP mice after injection of Lenti-CatB (12 mice) but not Lenti-NEP (7 mice) or Lenti-Control (5 mice). For each mouse, the extent of hippocampal plaques was expressed as the ratio of the percent area of thioflavin S-positive plaques on the injected versus uninjected side. *, $P<0.05$, Tukey Kramer post hoc test.

Example 2

Increasing the Activity Level of Cathepsin B

Figure 7:
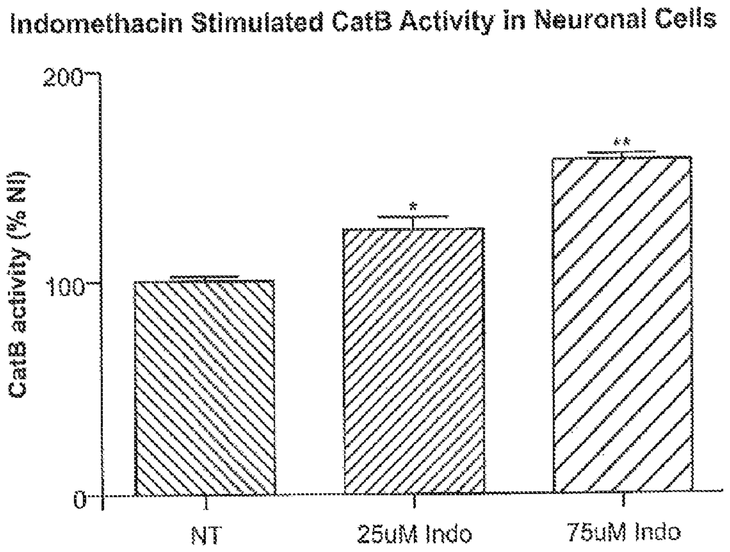
FIG. 7 depicts stimulation of CatB activity in neuronal cells by indomethacin.
Figure 8B:
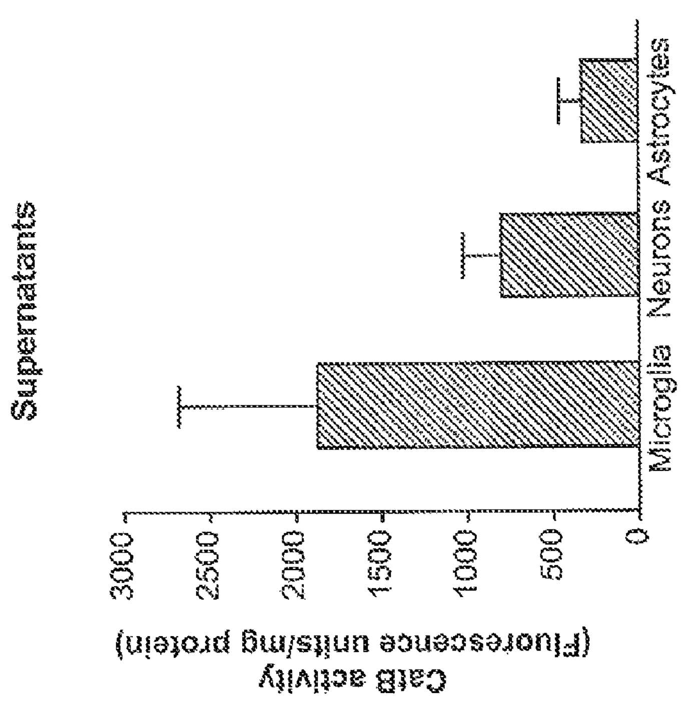
FIGS. 8A and 8B depict expression of CatB in glia and neurons.
Figure 8A:
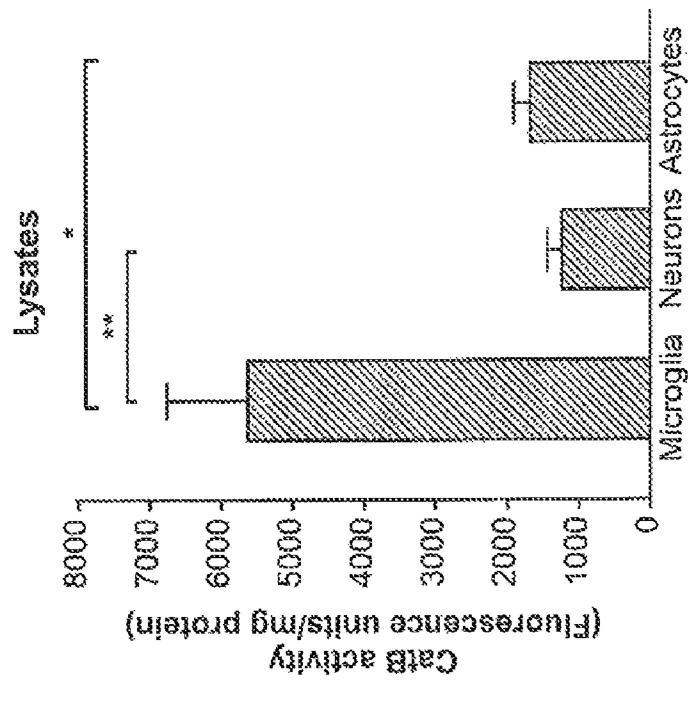

The data are depicted in FIG. 7 and FIGS. 8A and 8B. FIG. 7 shows that indomethacin stimulates cathepsin B activity in neuronal cells. FIGS. 8A and 8B show that cathepsin B is expressed in glia and neurons.

Neurobiatoma cell N2a cells were treated with indomethacin (25 μM-75 μM) for 18-24 h before being harvested for CatB activity assay. Treatment with indomethacin induced a significant increase in CatB activity in a dose-dependent manner (FIG. 7).

To determine the levels of enzymatically active CatB in different types of brain cells, cell lysates and supernatants were harvested from primary rat microglia, neuronal and astroglial cultures for CatB activity assays after 2 h of incubation in phosphate-buffered saline containing glucose. CatB activities were normalized to the protein concentrations in the cell lysates. Cat Values are means±S.E.M. (n=4-6; *, $P<0.05$, **, $P<0.01$, Tukey Kramer post hoc test). Interestingly, CatB activity was present in the supernatants of primary cultures enriched for neurons, astrocytes, or microglia; the highest levels were detected in microglial cultures. These results suggest that extracellular CatB accumulating within neuritic plaques could be produced by all three cell types, including activated microglia surrounding the plaques.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of increasing cathepsin B-induced cleavage of amyloid-β (Aβ) peptide in a neuron or a glial cell, the method comprising contacting the neuron or the glial cell with an agent that increases the level of cathepsin B-induced cleavage of Aβ in the neuron or the glial cell, wherein the agent is a non-steroidal anti-inflammatory agent.

2. The method of claim 1, wherein the cell is a neuron.

3. The method of claim 1, wherein the cell is a glial cell.

4. The method of claim 1, wherein the agent is indomethacin.

5. The method of claim 1, wherein the agent is ibuprofen.

6. The method of claim 1, wherein the agent is acetylsalicylic acid, sulindac, glucametacine, acemetacin, Nalfon, Naproxen, piroxicam, diclofenac, benoxaprofen, ketoprofen, oxaprozin, etodolac, ketorolac, or nabumetone.

7. The method of claim 1, wherein the Aβ is $A\beta_{1-42}$.

8. The method of claim 1, wherein the cathepsin B catalyzes carboxyl-terminal truncation of $A\beta_{1-42}$.

9. The method of claim 1, wherein the Aβ is cleaved at $Val_{40}$-$Ile_{41}$, $Gly_{38}$-$Gly_{39}$, or $Gly_{33}$-$Leu_{34}$.

10. The method of claim 1, wherein the cathepsin B generates $A\beta_{1-40}$, $A\beta_{1-38}$, and $A\beta_{1-33}$.

11. A method of increasing cathepsin B-induced cleavage of amyloid-β (Aβ) peptide in a neuron or a glial cell, the method comprising contacting the neuron or the glial cell with an agent that increases the level of cathepsin B-induced cleavage of Aβ in the neuron or the glial cell, wherein the agent is a non-steroidal anti-inflammatory agent selected from ibuprofen, indomethacin, acetylsalicylic acid, sulindac, glucametacine, acemetacin, Nalfon, Naproxen, piroxicam, diclofenac, benoxaprofen, ketoprofen, oxaprozin, etodolac, ketorolac, or nabumetone.

* * * * *

SEQUENCE LISTING

```
<160> NUMBER OF SEQ ID NOS: 11

<210> SEQ ID NO 1
<211> LENGTH: 2002
<212> TYPE: DNA
<213> ORGANISM: Homo sapiens

<400> SEQUENCE: 1

aattccgcgg caaccgctcc ggcaacgcca accgctccgc tgcgcgcagg ctgggctgca      60

ggctctcggc tgcagcgctg ggctggtgtg cagtggtgcg accacggctc acggcagcct     120

cagccaccca gatgtaagcg atctggttcc cacctcagcc ttccgagtag tggatctagg     180

atctggcttc caacatgtgg cagctctggg cctccctctg ctgcctgctg gtgttggcca     240

atgcccggag caggccctct ttccatcccg tgtcggatga gctggtcaac tatgtcaaca     300

aacggaatac cacgtggcag gccgggcaca acttctacaa cgtggacatg agctacttga     360

agaggctatg tggtaccttc ctgggtgggc ccaagccacc ccagagagtt atgtttaccg     420

aggacctgaa gctgcctgca agcttcgatg cacgggaaca atggccacag tgtcccacca     480

tcaaagagat cagagaccag ggctcctgtg gctcctgctg ggccttcggg gctgtggaag     540

ccatctctga ccgcatctgc atccacacca atgcgcacgt cagcgtggag gtgtcggcgg     600

aggacctgct cacctgctgt ggcagcatgt gtggggacgg ctgtaatggt ggctatcctg     660

ctgaagcttg gaacttctgg acaagaaaag gcctggtttc tggtggcctc tatgaatccc     720

atgtagggtg cagaccgtac tccatccctc cctgtgagca ccacgtcaac ggctcccggc     780

ccccatgcac gggggaggga gataccccca agtgtagcaa gatctgtgag cctggctaca     840

gcccgaccta caaacaggac aagcactacg gatacaattc ctacagcgtc tccaatagcg     900

agaaggacat catggccgag atctacaaaa acggccccgt ggagggagct ttctctgtgt     960

attcggactt cctgctctac aagtcaggag tgtaccaaca cgtcaccgga gagatgatgg    1020

gtggccatgc catccgcatc ctgggctggg gagtggagaa tggcacaccc tactggctgg    1080

ttgccaactc ctggaacact gactggggtg acaatggctt ctttaaaata ctcagaggac    1140
```

aggatcactg cggaatcgaa tcagaagtgg tggctggaat tccacgcacc gatcagtact 1200
gggaaaagat ctaatctgcc gtgggcctgt cgtgccagtc ctgggggcga gatcggggta 1260
gaaagtcatt ttattcttta agttcacgta agatacaagt ttcaggcagg gtctgaagga 1320
ctggattggc caaagtcctc caaggagacc aagtcctggc tacatcccag cctgtggtta 1380
cagtgcagac aggccatgtg agccaccgct gccagcacag agcgtccttc cccctgtaga 1440
ctagtgccgt gggagtacct gctgcccagc tgctgtggcc ccctccgtga tccatccatc 1500
tccagggagc aagacagaga cgcaggatgg aaagcggagt tcctaacagg atgaaagttc 1560
ccccatcagt tcccccagta cctccaagca agtagctttc cacatttgtc acagaaatca 1620
gaggagagat ggtgttggga gccctttgga gaacgccagt ctccaggtcc ccctgcatct 1680
atcgagtttg caatgtcaca acctctctga tcttgtgctc agcatgattc tttaatagaa 1740
gttttatttt tcgtgcactc tgctaatcat gtgggtgagc cagtggaaca gcgggagcct 1800
gtgctggttt gcagattgcc tcctaatgac gcggctcaaa aggaaaccaa gtggtcagga 1860
gttgtttctg acccactgat ctctactacc acaaggaaaa tagtttagga gaaaccagct 1920
tttactgttt ttgaaaaatt acagcttcac cctgtcaagt taacaaggaa tgcctgtgcc 1980
aataaaaggt ttctccaact tg 2002

<210> SEQ ID NO 2
<211> LENGTH: 339
<212> TYPE: PRT
<213> ORGANISM: Homo sapiens

<400> SEQUENCE: 2

Met Trp Gln Leu Trp Ala Ser Leu Cys Cys Leu Leu Val Leu Ala Asn
1 5 10 15

Ala Arg Ser Arg Pro Ser Phe His Pro Val Ser Asp Glu Leu Val Asn
20 25 30

Tyr Val Asn Lys Arg Asn Thr Thr Trp Gln Ala Gly His Asn Phe Tyr
35 40 45

Asn Val Asp Met Ser Tyr Leu Lys Arg Leu Cys Gly Thr Phe Leu Gly
50 55 60

Gly Pro Lys Pro Pro Gln Arg Val Met Phe Thr Glu Asp Leu Lys Leu
65 70 75 80

Pro Ala Ser Phe Asp Ala Arg Glu Gln Trp Pro Gln Cys Pro Thr Ile
85 90 95

Lys Glu Ile Arg Asp Gln Gly Ser Cys Gly Ser Cys Trp Ala Phe Gly
100 105 110

Ala Val Glu Ala Ile Ser Asp Arg Ile Cys Ile His Thr Asn Ala His
115 120 125

Val Ser Val Glu Val Ser Ala Glu Asp Leu Leu Thr Cys Cys Gly Ser
130 135 140

Met Cys Gly Asp Gly Cys Asn Gly Gly Tyr Pro Ala Glu Ala Trp Asn
145 150 155 160

Phe Trp Thr Arg Lys Gly Leu Val Ser Gly Gly Leu Tyr Glu Ser His
165 170 175

Val Gly Cys Arg Pro Tyr Ser Ile Pro Pro Cys Glu His His Val Asn
180 185 190

Gly Ser Arg Pro Pro Cys Thr Gly Glu Gly Asp Thr Pro Lys Cys Ser
195 200 205

Lys Ile Cys Glu Pro Gly Tyr Ser Pro Thr Tyr Lys Gln Asp Lys His
210 215 220

Tyr Gly Tyr Asn Ser Tyr Ser Val Ser Asn Ser Glu Lys Asp Ile Met
225 230 235 240

Ala Glu Ile Tyr Lys Asn Gly Pro Val Glu Gly Ala Phe Ser Val Tyr
245 250 255

Ser Asp Phe Leu Leu Tyr Lys Ser Gly Val Tyr Gln His Val Thr Gly
260 265 270

Glu Met Met Gly Gly His Ala Ile Arg Ile Leu Gly Trp Gly Val Glu
275 280 285

Asn Gly Thr Pro Tyr Trp Leu Val Ala Asn Ser Trp Asn Thr Asp Trp
290 295 300

Gly Asp Asn Gly Phe Phe Lys Ile Leu Arg Gly Gln Asp His Cys Gly
305 310 315 320

Ile Glu Ser Glu Val Val Ala Gly Ile Pro Arg Thr Asp Gln Tyr Trp
325 330 335

Glu Lys Ile

<210> SEQ ID NO 3
<211> LENGTH: 247
<212> TYPE: PRT
<213> ORGANISM: Pan troglodytes

<400> SEQUENCE: 3

Met Glu Glu Asp Gly Pro Asn Val Ala Lys Met Asp Val Gly Leu Leu
1 5 10 15

Trp Leu Thr Leu Tyr Asn Ile Pro Leu Ile Gly Val Phe Arg Pro Met
20 25 30

Glu Ser Ser Leu Arg Gly Leu Gly Leu Gln Tyr Leu Val Cys Ile Asp
35 40 45

Asp Gly Gln Val Gly Ser Thr Gly Lys Asp Leu Cys Arg Glu Pro Ala
50 55 60

Pro Trp Asp Arg Trp Ala Ser Asp Leu Arg Cys Ser Asn Ala Arg Ser
65 70 75 80

Arg Pro Ser Phe His Pro Leu Ser Asp Glu Leu Val Asn Tyr Val Asn
85 90 95

Lys Arg Asn Thr Thr Trp Gln Ala Gly His Asn Phe Tyr Asn Val Asp
100 105 110

Met Ser Tyr Leu Lys Arg Leu Cys Gly Ala Phe Leu Gly Gly Pro Lys
115 120 125

Pro Pro Gln Arg Val Met Phe Thr Glu Asp Leu Lys Leu Pro Glu Ser
130 135 140

Phe Asp Ala Arg Glu Gln Trp Pro Gln Cys Pro Thr Ile Lys Glu Ile
145 150 155 160

Arg Asp Gln Gly Ser Cys Gly Ser Cys Trp Ala Phe Gly Ala Val Glu
165 170 175

Ala Ile Ser Asp Arg Ile Cys Ile His Thr Asn Ala His Val Ser Val
180 185 190

Glu Val Ser Ala Glu Asp Leu Leu Thr Cys Cys Gly Ser Met Cys Gly
195 200 205

Asp Gly Cys Asn Gly Gly Tyr Pro Ala Glu Ala Trp Asn Phe Trp Thr
210 215 220

Arg Lys Gly Leu Val Ser Gly Gly Leu Tyr Glu Ser His Val Gly Cys
225 230 235 240

Arg Pro Tyr Ser Ile Pro Pro
245

-continued

<210> SEQ ID NO 4
<211> LENGTH: 339
<212> TYPE: PRT
<213> ORGANISM: Mus musculus

<400> SEQUENCE: 4

```
Met Trp Trp Ser Leu Ile Leu Leu Ser Cys Leu Leu Ala Leu Thr Ser
1               5                   10                  15

Ala His Asp Lys Pro Ser Phe His Pro Leu Ser Asp Asp Leu Ile Asn
            20                  25                  30

Tyr Ile Asn Lys Gln Asn Thr Thr Trp Gln Ala Gly Arg Asn Phe Tyr
        35                  40                  45

Asn Val Asp Ile Ser Tyr Leu Lys Lys Leu Cys Gly Thr Val Leu Gly
    50                  55                  60

Gly Pro Lys Leu Pro Gly Arg Val Ala Phe Gly Glu Asp Ile Asp Leu
65                  70                  75                  80

Pro Glu Thr Phe Asp Ala Arg Glu Gln Trp Ser Asn Cys Pro Thr Ile
                85                  90                  95

Gly Gln Ile Arg Asp Gln Gly Ser Cys Gly Ser Cys Trp Ala Phe Gly
            100                 105                 110

Ala Val Glu Ala Ile Ser Asp Arg Thr Cys Ile His Thr Asn Gly Arg
        115                 120                 125

Val Asn Val Glu Val Ser Ala Glu Asp Leu Leu Thr Cys Cys Gly Ile
    130                 135                 140

Gln Cys Gly Asp Gly Cys Asn Gly Gly Tyr Pro Ser Gly Ala Trp Ser
145                 150                 155                 160

Phe Trp Thr Lys Lys Gly Leu Val Ser Gly Gly Val Tyr Asn Ser His
                165                 170                 175

Val Gly Cys Leu Pro Tyr Thr Ile Pro Pro Cys Glu His His Val Asn
            180                 185                 190

Gly Ser Arg Pro Pro Cys Thr Gly Glu Gly Asp Thr Pro Arg Cys Asn
        195                 200                 205

Lys Ser Cys Glu Ala Gly Tyr Ser Pro Ser Tyr Lys Glu Asp Lys His
    210                 215                 220

Phe Gly Tyr Thr Ser Tyr Ser Val Ser Asn Ser Val Lys Glu Ile Met
225                 230                 235                 240

Ala Glu Ile Tyr Lys Asn Gly Pro Val Glu Gly Ala Phe Thr Val Phe
                245                 250                 255

Ser Asp Phe Leu Thr Tyr Lys Ser Gly Val Tyr Lys His Glu Ala Gly
            260                 265                 270

Asp Met Met Gly Gly His Ala Ile Arg Ile Leu Gly Trp Gly Val Glu
        275                 280                 285

Asn Gly Val Pro Tyr Trp Leu Ala Ala Asn Ser Trp Asn Leu Asp Trp
    290                 295                 300

Gly Asp Asn Gly Phe Phe Lys Ile Leu Arg Gly Glu Asn His Cys Gly
305                 310                 315                 320

Ile Glu Ser Glu Ile Val Ala Gly Ile Pro Arg Thr Asp Gln Tyr Trp
                325                 330                 335

Gly Arg Phe
```

<210> SEQ ID NO 5
<211> LENGTH: 339
<212> TYPE: PRT
<213> ORGANISM: Rattus norvegicus

<400> SEQUENCE: 5

-continued

```
Met Trp Trp Ser Leu Ile Pro Leu Ser Cys Leu Leu Ala Leu Thr Ser
1               5                   10                  15

Ala His Asp Lys Pro Ser Phe His Pro Leu Ser Asp Asp Met Ile Asn
            20                  25                  30

Tyr Ile Asn Lys Gln Asn Thr Thr Trp Gln Ala Gly Arg Asn Phe Tyr
        35                  40                  45

Asn Val Asp Ile Ser Tyr Leu Lys Lys Leu Cys Gly Thr Val Leu Gly
    50                  55                  60

Gly Pro Lys Leu Pro Glu Arg Val Gly Phe Ser Glu Asp Ile Asn Leu
65                  70                  75                  80

Pro Glu Ser Phe Asp Ala Arg Glu Gln Trp Ser Asn Cys Pro Thr Ile
                85                  90                  95

Ala Gln Ile Arg Asp Gln Gly Ser Cys Gly Ser Cys Trp Ala Phe Gly
            100                 105                 110

Ala Val Glu Ala Met Ser Asp Arg Ile Cys Ile His Thr Asn Gly Arg
        115                 120                 125

Val Asn Val Glu Val Ser Ala Glu Asp Leu Leu Thr Cys Cys Gly Ile
    130                 135                 140

Gln Cys Gly Asp Gly Cys Asn Gly Gly Tyr Pro Ser Gly Ala Trp Asn
145                 150                 155                 160

Phe Trp Thr Arg Lys Gly Leu Val Ser Gly Gly Val Tyr Asn Ser His
                165                 170                 175

Ile Gly Cys Leu Pro Tyr Thr Ile Pro Pro Cys Glu His His Val Asn
            180                 185                 190

Gly Ser Arg Pro Pro Cys Thr Gly Glu Gly Asp Thr Pro Lys Cys Asn
        195                 200                 205

Lys Met Cys Glu Ala Gly Tyr Ser Thr Ser Tyr Lys Glu Asp Lys His
    210                 215                 220

Tyr Gly Tyr Thr Ser Tyr Ser Val Ser Asp Ser Glu Lys Glu Ile Met
225                 230                 235                 240

Ala Glu Ile Tyr Lys Asn Gly Pro Val Glu Gly Ala Phe Thr Val Phe
                245                 250                 255

Ser Asp Phe Leu Thr Tyr Lys Ser Gly Val Tyr Lys His Glu Ala Gly
            260                 265                 270

Asp Val Met Gly Gly His Ala Ile Arg Ile Leu Gly Trp Gly Ile Glu
        275                 280                 285

Asn Gly Val Pro Tyr Trp Leu Val Ala Asn Ser Trp Asn Val Asp Trp
    290                 295                 300

Gly Asp Asn Gly Phe Phe Lys Ile Leu Arg Gly Glu Asn His Cys Gly
305                 310                 315                 320

Ile Glu Ser Glu Ile Val Ala Gly Ile Pro Arg Thr Gln Gln Tyr Trp
                325                 330                 335

Gly Arg Phe
```

<210> SEQ ID NO 6
<211> LENGTH: 340
<212> TYPE: PRT
<213> ORGANISM: Gallus gallus

<400> SEQUENCE: 6

```
Met Ser Trp Ser Arg Ser Ile Leu Cys Leu Leu Gly Ala Phe Ala Asn
1               5                   10                  15

Ala Arg Ser Ile Pro Tyr Tyr Pro Pro Leu Ser Ser Asp Leu Val Asn
            20                  25                  30
```

```
His Ile Asn Lys Leu Asn Thr Thr Gly Arg Ala Gly His Asn Phe His
        35                  40                  45

Asn Thr Asp Met Ser Tyr Val Lys Lys Leu Cys Gly Thr Phe Leu Gly
    50                  55                  60

Gly Pro Lys Ala Pro Glu Arg Val Asp Phe Ala Glu Asp Met Asp Leu
65                  70                  75                  80

Pro Asp Thr Phe Asp Thr Arg Lys Gln Trp Pro Asn Cys Pro Thr Ile
                85                  90                  95

Ser Glu Ile Arg Asp Gln Gly Ser Cys Gly Ser Cys Trp Ala Phe Gly
            100                 105                 110

Ala Val Glu Ala Ile Ser Asp Arg Ile Cys Val His Thr Asn Ala Lys
        115                 120                 125

Val Ser Val Glu Val Ser Ala Glu Asp Leu Leu Ser Cys Cys Gly Phe
    130                 135                 140

Glu Cys Gly Met Gly Cys Asn Gly Gly Tyr Pro Ser Gly Ala Trp Arg
145                 150                 155                 160

Tyr Trp Thr Glu Arg Gly Leu Val Ser Gly Gly Leu Tyr Asp Ser His
                165                 170                 175

Val Gly Cys Arg Ala Tyr Thr Ile Pro Pro Cys Glu His His Val Asn
            180                 185                 190

Gly Ser Arg Pro Pro Cys Thr Gly Glu Gly Gly Glu Thr Pro Arg Cys
        195                 200                 205

Ser Arg His Cys Glu Pro Gly Tyr Ser Pro Ser Tyr Lys Glu Asp Lys
    210                 215                 220

His Tyr Gly Ile Thr Ser Tyr Gly Val Pro Arg Ser Glu Lys Glu Ile
225                 230                 235                 240

Met Ala Glu Ile Tyr Lys Asn Gly Pro Val Glu Gly Ala Phe Ile Val
                245                 250                 255

Tyr Glu Asp Phe Leu Met Tyr Lys Ser Gly Val Tyr Gln His Val Ser
            260                 265                 270

Gly Glu Gln Val Gly Gly His Ala Ile Arg Ile Leu Gly Trp Gly Val
        275                 280                 285

Glu Asn Gly Thr Pro Tyr Trp Leu Ala Ala Asn Ser Trp Asn Thr Asp
    290                 295                 300

Trp Gly Ile Thr Gly Phe Phe Lys Ile Leu Arg Gly Glu Asp His Cys
305                 310                 315                 320

Gly Ile Glu Ser Glu Ile Val Ala Gly Val Pro Arg Met Glu Gln Tyr
                325                 330                 335

Trp Thr Arg Val
            340


<210> SEQ ID NO 7
<211> LENGTH: 21
<212> TYPE: DNA
<213> ORGANISM: Artificial Sequence
<220> FEATURE:
<223> OTHER INFORMATION: Synthetic Primer

<400> SEQUENCE: 7

tggtttcagg tggagtctac a                                              21


<210> SEQ ID NO 8
<211> LENGTH: 21
<212> TYPE: DNA
<213> ORGANISM: Artificial Sequence
<220> FEATURE:
<223> OTHER INFORMATION: Synthetic Primer
```

-continued

```
<400> SEQUENCE: 8

tgcactggag aaggagatac t                                              21


<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9

gggaagccca tcaccatctt                                                20


<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10

gccttctcca tggtggtgaa                                                20


<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11

gaagctgtgt ggcactgtc                                                 19
```